(12) United States Patent
Maxwell et al.

(10) Patent No.: US 9,035,267 B2
(45) Date of Patent: May 19, 2015

(54) IN-LINE PHOTOLUMINESCENCE IMAGING OF SEMICONDUCTOR DEVICES

(75) Inventors: Ian A. Maxwell, Five Dock (AU); Thorsten Trupke, Coogee (AU); Robert A. Bardos, Surry Hills (AU); Kenneth E. Arnett, Boulder, CO (US)

(73) Assignee: BT IMAGING PTY LTD, Redfern (AU)

( * ) Notice: Subject to any disclaimer, the term of this patent is extended or adjusted under 35 U.S.C. 154(b) by 200 days.

(21) Appl. No.: 13/520,375

(22) PCT Filed: Jan. 4, 2011

(86) PCT No.: PCT/AU2011/000005
§ 371 (c)(1),
(2), (4) Date: Oct. 26, 2012

(87) PCT Pub. No.: WO2011/079354
PCT Pub. Date: Jul. 7, 2011

(65) Prior Publication Data
US 2013/0043405 A1    Feb. 21, 2013

(30) Foreign Application Priority Data

Jan. 4, 2010 (AU) ............................... 2010900018
Jul. 9, 2010 (AU) ............................... 2010903050
Sep. 3, 2010 (AU) ............................... 2010903975

(51) Int. Cl.
*G01N 21/64* (2006.01)

(52) U.S. Cl.
CPC ................................ *G01N 21/6489* (2013.01)

(58) Field of Classification Search
CPC ........................................................ G01N 21/64
USPC ......................................................... 250/458.1
See application file for complete search history.

(56) References Cited

U.S. PATENT DOCUMENTS

| 8,064,054 B2 | 11/2011 | Trupke et al. |
| 2002/0030826 A1 | 3/2002 | Chalmers et al. |
| 2005/0174583 A1* | 8/2005 | Chalmers et al. ............ 356/630 |

(Continued)

FOREIGN PATENT DOCUMENTS

| EP | 1801569 A3 | 7/2008 |
| EP | 2284520 A1 | 2/2011 |
| WO | WO-2010/007617 A3 | 3/2010 |

OTHER PUBLICATIONS

International Search Report for PCT/AU2011/000005 filing Apr. 8, 2011.

*Primary Examiner* — David Porta
*Assistant Examiner* — Hugh H Maupin
(74) *Attorney, Agent, or Firm* — Mattingly & Malur, PC

(57) ABSTRACT

Methods and systems are presented for acquiring photoluminescence images (2) of silicon solar cells and wafers (4) as they progress along a manufacturing line (36). In preferred embodiments the images are acquired while maintaining motion of the samples. In certain embodiments photoluminescence is generated with short pulse, high intensity excitation, (8) for instance by a flash lamp (50) while in other embodiments images are acquired in line scanning fashion. The photoluminescence images can be analysed to obtain information on average or spatially resolved values of one or more sample properties such as minority carrier diffusion length, minority carrier lifetime, dislocation defects, impurities and shunts, or information on the incidence or growth of cracks in a sample.

65 Claims, 10 Drawing Sheets

(56) References Cited

U.S. PATENT DOCUMENTS

| | | |
|---|---|---|
| 2007/0048884 A1 | 3/2007 | Nagel |
| 2010/0006785 A1 | 1/2010 | Finarov |
| 2010/0074515 A1* | 3/2010 | Zhao et al. .................. 382/149 |
| 2010/0220316 A1 | 9/2010 | Finarov |
| 2011/0025839 A1* | 2/2011 | Trupke et al. .................. 348/87 |
| 2012/0142125 A1 | 6/2012 | Trupke et al. |

* cited by examiner

IN-LINE PHOTOLUMINESCENCE IMAGING OF SEMICONDUCTOR DEVICES

FIELD OF THE INVENTION

The present invention relates to methods and systems for performing photoluminescence analyses of semiconductor devices, and of silicon solar cells in particular, during or after their production process.

RELATED APPLICATIONS

The present application is a 371 national stage application of PCT/AU2011/000005, filed Jan. 4, 2011, which claims priority to AU 2010900018 filed Jan. 4, 2010, AU 2010903050filed Jul. 9, 2010, and AU 2010903975 filed Sep. 3, 2010. The entire contents of each of these applications are hereby incorporated by reference.

BACKGROUND OF THE INVENTION

Any discussion of the prior art throughout this specification should in no way be considered as an admission that such prior art is widely known or forms part of the common general knowledge in the field.

Photoluminescence (PL) imaging, performed for example using apparatus and methods disclosed in PCT Patent Application Publication No WO 2007/041758 A1 entitled 'Method and System for Inspecting Indirect Bandgap Semiconductor Structure' and incorporated herein by reference, has been shown to be of value for the rapid characterisation of silicon materials and devices, and silicon wafer-based solar cells in particular. As shown schematically in FIG. 1, luminescence 2 generated from a semiconductor sample 4 with broad area photo-excitation from a source 6 of above-bandgap light 8 can be imaged with a camera or CCD array 10 via collection optics 11, with the system preferably including homogenisation optics 12 to improve the uniformity of the broad area excitation and a long-pass filter 14 in front of the camera to block excitation light. The system may also include one or more filters 15 to select the wavelength range of the photo-excitation. With relatively thin samples it is also possible to have the excitation source 6 and camera 10 on opposite sides of the sample 4 as shown in FIG. 2, in which case the sample itself can serve as a long-pass filter. However a long-pass filter 14 may still be required if a significant amount of stray excitation light, reflected for example off other components, is reaching the camera. Either way, the acquired PL image can be analysed with a computer 16, using techniques disclosed for example in published PCT patent application Nos WO 2008/014537 A1, WO 2009/026661 A1 and WO 2009/121133 A1, to obtain information on average or spatially resolved values of a number of sample properties including minority carrier diffusion length, minority carrier lifetime, dislocation defects, impurities and shunts, amongst others, or on the incidence or growth of cracks. In principle the entire process can be performed in a matter of seconds or fractions of a second depending on factors such as the quality of silicon material and the readout speed of the camera, which is a timescale generally compatible with current solar block, cell and wafer production lines where, for example, the throughput for wafer and cell lines is of order one cell per second or two, and for block production where 30 seconds is typically available for the measurement of a full block face.

However the current PL imaging system as described above suffers from a number of disadvantages.

One disadvantage is that currently available PL imaging systems require samples to be removed from production lines and taken to the PL imaging tool, for example using robotic or manual pick and place handling. Manual pick and place handling is a labour intensive and slow process that often adds cost as well as being slow, and although robotic pick and place handling systems using platens or suction cups or similar are somewhat faster, they also add cost. Either way, the limited speed means only a small sample of the product in process can be tested. It would be beneficial to be able to measure all or most of the work product.

A further disadvantage is that in current PL imaging systems the sample has to be stationary during the measurement to prevent blurring of the image. A blurred image can prevent or compromise the capture of spatially resolved characterisation data, complicating the design and/or incorporation of a PL imaging system into production lines that are increasingly operating in continuous mode without stopping. To explain, with broad area 1 Sun excitation the photoluminescence emitted from many silicon samples, and raw or unpassivated silicon samples in particular, can be of such low intensity that even the most sensitive commercially available silicon-based CCD cameras require an exposure time of order at least 0.5 second to acquire a sufficient PL signal.

Yet another disadvantage with current PL imaging systems is the common reliance on laser excitation sources, typically in the near IR region of the spectrum. To explain, obtaining a measurable PL signal from low photoluminescence quantum efficiency samples such as raw or unpassivated silicon wafers and blocks (with quantum efficiency of order $10^{-6}$) often requires illumination intensities of 0.1 Watts/cm$^2$ (~1 Sun) or greater. A total optical power of tens of Watts is therefore required to illuminate silicon solar cell wafers that may typically be 15.6×15.6 cm$^2$ in area, and laser excitation sources are usually considered to be essential to provide the required spectral purity and beam shaping. Furthermore for silicon samples the excitation light is typically in the near IR region (750 to 1000 nm), which is potentially very harmful because the eye focuses near-infrared light onto the retina but its protective 'blink reflex' response is triggered only by visible light. The potential hazard of laser light sources arises from the fact that they may be much brighter than other light sources, where the brightness (in units of power per unit area per unit solid angle) may be defined for example as the optical power passing through an aperture (e.g. a laser output aperture) divided by the aperture area divided by the solid angle subtended by the optical beam in the far field. When an extremely bright light source is viewed with the eye, either directly or via intermediate optics such as a collimating lens, the image formed on the retina can be extremely intense, resulting in virtually instantaneous and permanent damage. However although there is less likelihood of this occurring with incoherent near IR light, e.g. from high power LEDs, it needs to be understood that because brightness is a key parameter, light safety issues cannot simply be ignored just because a system uses non-laser (incoherent) light sources.

Current PL imaging systems are therefore further complicated by light safety issues, since the PL measurement chamber generally must be optically isolated to avoid the risk of operators being exposed to high brightness IR light that could cause eye damage. This usually requires shutters, doors or equivalent mechanisms, adding complexity and cost to the sample transfer mechanisms into and out of the PL measurement chamber. Because of these complications, the basic PL imaging apparatus shown in FIG. 1 or 2 requires several modifications if it is to be used safely and cost effectively to characterise silicon solar cells on a production line.

SUMMARY OF THE INVENTION

It is an object of the present invention to overcome or ameliorate at least one of the disadvantages of the prior art, or to provide a useful alternative. It is an object of a preferred form of the present invention to provide methods and systems for acquiring photoluminescence images of semiconductor devices during their production process without removing them from the production line. It is another object of a preferred form of the present invention to provide methods and systems for acquiring photoluminescence images of semiconductor devices during their production process without interrupting the motion of the devices through the production line. It is another object of a preferred form of the present invention to provide methods and systems for acquiring photoluminescence images of semiconductor devices using imaging systems that are eye-safe without requiring light safety shutters. It is another object of a preferred form of the present invention to provide methods and systems for acquiring photoluminescence images of silicon wafers or cells with a total measurement time between 0.1 and 1 second per wafer or cell. It is another object of a preferred form of the present invention to provide a photoluminescence imaging system that does not have or require an integrated sample handling stage.

According to a first aspect the invention provides a method for analysing a sample of a semiconductor material, said method comprising the steps of:

passing said sample to a measurement zone;

applying an illumination to said semiconductor material to produce a photoluminescence response; and conducting at least a photoluminescence analysis of said sample in said measurement zone while maintaining motion of said sample.

According to a second aspect of the invention provides a method of conducting a photoluminescence analysis of a sample of a semiconductor material moving through a measurement zone, said method comprising the steps of: applying an illumination to the semiconductor material for a sufficient time and intensity to produce a photoluminescence response; and capturing an image of the photoluminescence emanating from said semiconductor material, wherein said image capture is obtained within a distance of up to 1 or 2 pixels of the imaging camera.

Preferably, said photoluminescence analysis comprises the steps of:

illuminating an area of said sample with a predetermined illumination to generate photoluminescence from said sample in response to said illumination; and acquiring an image of said photoluminescence with an area image capture device in an acquisition time t, wherein said sample is moving at a speed v relative to said area image capture device, and wherein the product of the acquisition time t (s) and the speed v (m·s$^{-1}$) is less than a distance on said sample corresponding to one row of pixels in said image capture device.

Preferably said illumination comprises incoherent light. Said illumination may comprise a pulse of light.

Preferably, said photoluminescence analysis comprises the steps of:

providing a source of predetermined illumination suitable for generating photoluminescence from said sample, said source being positioned so as to illuminate a first portion of said sample;

providing an image capture device for detecting the photoluminescence emitted from a second portion of said sample, wherein said first portion and said second portion are at least partially overlapping;

moving said sample relative to said source and to said image capture device such that said second portion is scanned across a substantial area of said sample; and interrogating said image capture device repeatedly to acquire an image of the photoluminescence emitted from said area.

Preferably said illumination comprises incoherent light.

Preferably the image capture device is a line camera.

Preferably said first portion is from one to five times wider than said second portion in the direction of movement of said sample.

Alternatively, the image capture device is a time-delayed integration camera.

In one embodiment said first portion is substantially coterminous with said second portion. In another embodiment, said first portion is wholly or partially within said second portion. In yet another embodiment, said second portion is wholly or partially within said first portion.

Preferably, said first and second portions extend across a substantial fraction of a dimension of said sample, said dimension being substantially perpendicular to the direction of movement of said sample.

The semiconductor material may be raw or unpassivated silicon. In that case, it is preferred if said photoluminescence is generated with an illumination intensity between about 1 and 40 W·cm$^{-2}$.

Alternatively, said semiconductor material may be passivated silicon. In that case, it is preferred if said photoluminescence is generated with an illumination intensity between about 0.1 and 10 W·cm$^{-2}$.

Preferably the illumination source and/or an optical element associated therewith moves within the measurement zone. In that case, it is preferred that motion of the illumination source and/or an optical element associated therewith is controlled to maintain a predetermined alignment with a sample. The predetermined alignment may be to avoid blurring of illumination of the sample.

Preferably, the image capture device and/or an optical element associated therewith moves within the measurement zone. In that case, it is preferred that motion of the image capture device and/or an optical element associated therewith is controlled to maintain a predetermined alignment with a sample. The predetermined alignment may be to avoid blurring of image capture of the sample.

Preferably, illumination is introduced into the imaging optical system using a dichroic mirror. In that case, it is preferred if photoluminescence data captured passes through said dichroic mirror.

Preferably said photoluminescence analysis provides information on average or spatially resolved values of one or more properties of said sample, said properties being selected from the group consisting of minority carrier diffusion length, minority carrier lifetime, dislocation defects, impurities and shunts.

Preferably said sample is a silicon wafer.

Preferably said analysis is performed in less than 1 second.

In one embodiment, the configuration of the measurement zone remains constant before, during and after data acquisition. The measurement zone may be a shuttered or enclosed chamber. Alternatively, said measurement zone is unenclosed.

According to a third aspect the invention provides a method for analysing a sample of a semiconductor material, said method comprising the steps of:

passing said sample to a measurement zone; and conducting at least a photoluminescence analysis of said sample in said measurement zone, wherein said measurement zone is eye-safe without being enclosed.

According to a fourth aspect the invention provides a method for analysing a sample of a semiconductor material, said method comprising the steps of:

passing said sample to a measurement zone without using a pick and place sample handling system; and conducting at least a photoluminescence analysis of said sample in said measurement zone.

According to a fifth aspect the invention provides a system for conducting an analysis of a sample of a semiconductor material, said apparatus comprising:

a transport mechanism for transporting said sample to a measurement zone;

analysis equipment for conducting at least a photoluminescence analysis of said sample within said measurement zone; and motion apparatus to maintain motion of said sample within said measurement zone during said analysis.

Preferably said analysis equipment comprises:

an optical source for illuminating an area of said sample with a predetermined illumination to generate photoluminescence from said sample in response to said illumination; and an area image capture device for capturing an image of said photoluminescence in an image acquisition time t, wherein said motion apparatus moves said sample at a speed v relative to said area image capture device such that the product of the image acquisition time t (s) and the speed v (m·s$^{-1}$) is less than a distance on said sample corresponding to one row of pixels in said area image capture device.

Preferably said analysis equipment comprises:

a source of predetermined illumination suitable for generating photoluminescence from said sample, said source being positioned so as to illuminate a first portion of said sample;

an image capture device for detecting the photoluminescence generated from a second portion of said sample, wherein said first portion and said second portion are at least partially overlapping; and means for interrogating said image capture device repeatedly while said motion means moves said sample such that said second portion is scanned across a substantial area of said sample, to acquire an image of the photoluminescence emitted from said area.

Preferably the illumination source and/or an optical element associated therewith moves within the measurement zone. In that case, it is preferred that motion of the illumination source and/or an optical element associated therewith is controlled to maintain a predetermined alignment with a sample. The predetermined alignment may be to avoid blurring of illumination of the sample.

Preferably, the image capture device and/or an optical element associated therewith moves within the measurement zone. In that case, it is preferred that motion of the image capture device and/or an optical element associated therewith is controlled to maintain a predetermined alignment with a sample. The predetermined alignment may be to avoid blurring of image capture of the sample.

Preferably, illumination is introduced into the imaging optical system using a dichroic mirror. In that case, it is preferred if the photoluminescence passes through said dichroic mirror prior to image capture.

Preferably the configuration of the measurement zone remains constant before, during and after data acquisition.

In one embodiment, said measurement zone is a shuttered or enclosed chamber. In an alternative embodiment said measurement zone is unenclosed.

According to a sixth aspect the invention provides a system for conducting an analysis of a sample of a semiconductor material, said system comprising:

a transport mechanism for transporting said sample to a measurement zone;

a light source for illuminating an area of said sample to generate photoluminescence from said sample; and analysis equipment for conducting at least a photoluminescence analysis of said sample within said measurement zone, wherein said measurement zone is eye-safe without being enclosed.

According to a seventh aspect the invention provides a system for conducting an analysis of a sample of a semiconductor material, said system comprising:

a transport mechanism for transporting said sample to a measurement zone without using a pick and place sample handling system; and analysis equipment for conducting at least a photoluminescence analysis of said sample in said measurement zone.

According to a eighth aspect the invention provides a method of analysing a sample of semiconductor material from within a series of samples of semiconductor material, said method comprising the steps of:

passing said sample to a measurement zone; and acquiring photoluminescence data from said sample in said measurement zone while enabling motion of other samples in said series of samples.

In one embodiment said sample is in motion during acquisition of photoluminescence data.

In an alternative embodiment said sample is stationary during acquisition of photoluminescence data.

The other samples in said series of samples may be in motion during acquisition of photoluminescence data, or alternatively, the other samples in said series of samples are not in motion during acquisition of photoluminescence data.

According to a ninth aspect the invention provides a method of analysing a sample of semiconductor material, said method comprising the steps of:

conveying said sample to a point adjacent to a measurement zone by a delivery transport means;

conveying said sample into, through and out of said measurement zone by a measurement zone transport means;

acquiring photoluminescence data from said sample in said measurement zone; and conveying said sample from a point adjacent the measurement zone by a removal transport means, wherein the measurement zone transport means is controllable independently of said delivery transport means or said removal transport means.

In one embodiment, the measurement zone transport means and/or sample is motionless during the acquisition of photoluminescence data.

In an alternative embodiment, the measurement zone transport means and/or sample is in motion during the acquisition of photoluminescence data.

Preferably said photoluminescence is generated by illumination with incoherent light.

Preferably said photoluminescence is generated by illumination comprising a pulse of light.

In one embodiment, analysing a sample of semiconductor material takes place in a shuttered or enclosed analysis chamber.

In an alternative embodiment, analysing a sample of semiconductor material takes place in an unshuttered or at least partially open analysis chamber.

Preferably the sample is illuminated by illumination introduced using a dichroic mirror.

Preferably the acquired photoluminescence data is analysed to obtain information on average or spatially resolved values of a sample property selected from the group consisting of minority carrier diffusion length, minority carrier lifetime, dislocation defects, impurities and shunts.

Preferably said sample is a silicon wafer.
Preferably said analysis is performed in less than 1 second.

According to a tenth aspect the invention provides a method for analysing a sample of a semiconductor material in a measurement zone, said method comprising a transport mechanism for moving and supporting said sample, wherein said transport mechanism contacts no more than 10% of said sample, thereby leaving 90% of said sample exposed at all times for analysis.

According to a eleventh aspect the invention provides a method for analysing a sample of a semiconductor material in a measurement zone, said method comprising a transport mechanism for movement and support of said sample during analysis wherein during said analysis at least a portion of said sample is left unsupported across its entire width to provide an unobstructed region for said analysis whereby, as a result of continued movement, the entire sample is progressively unobstructed.

According to a twelfth aspect the invention provides a system for analysing a sample of semiconductor material, said system comprising:
a delivery transport means to convey said sample to a point adjacent to a measurement zone;
a measurement zone transport means for conveying said sample into, through and out of said measurement zone;
an illumination means for generating photoluminescence from said sample in said measurement zone;
a detector for detecting said photoluminescence; and
a removal transport means for conveying said sample from a point adjacent the measurement zone, wherein the measurement zone transport means is controllable independently of said delivery transport means or said removal transport means.

Preferably said illumination means emits incoherent light.
Preferably said illumination means emits a pulse of light.
Preferably the delivery transport means, measurement zone transport means and removal transport means are independently selected from the group consisting of a belt, a series of rollers, a series of platens, a plurality of aligned belts and a vacuum chuck.

Preferably the measurement zone transport means is a plurality of aligned belts configured to support opposed sides of a semiconductor sample, the area between said belts defining an unobstructed central portion of the semiconductor sample.

Preferably light from the illumination means is introduced to the sample using a dichroic mirror.

In one embodiment, analysing a sample of semiconductor material takes place in a shuttered or enclosed analysis chamber.

In an alternative embodiment, analysing a sample of semiconductor material takes place in an unshuttered or at least partially open analysis chamber.

Preferably the delivery transport means, the measurement zone transport means and the removal transport means do not use a pick and place sample handling system.

Preferably an acquired photoluminescence image is analysed to obtain information on average or spatially resolved values of a sample property selected from the group consisting of minority carrier diffusion length, minority carrier lifetime, dislocation defects, impurities and shunts.

Preferably said sample is a silicon wafer.
Preferably said analysis is performed in less than 1 second.

According to a thirteenth aspect the invention provides a system for analysing a sample of a semiconductor material in a measurement zone, said system comprising a transport mechanism for moving and supporting said sample, wherein said transport mechanism contacts no more than 10% of said sample, thereby leaving 90% of said sample exposed at all times for analysis.

According to a fourteenth aspect the invention provides a system for analysing a sample of a semiconductor material in a measurement zone, said system comprising a transport mechanism for movement and support of said sample during analysis wherein during said analysis at least a portion of said sample is left unsupported across its entire width to provide an unobstructed region for said analysis whereby, as a result of continued movement, the entire sample is progressively unobstructed.

According to a fifteenth aspect, the present invention provides a production line for the production of a photovoltaic device, said production line comprising a plurality of process steps to convert a semiconductor material to said photovoltaic device, said production line including at least one analysis device comprising a illumination source for application to a semiconductor material, and a non-stop image capture device for obtaining an image of photoluminescence emanating from said illuminated semiconductor material without stopping the semiconductor material.

According to a sixteenth aspect, the present invention provides a production line for the production of photovoltaic device, said production line comprising a plurality of process steps to convert a semiconductor material to said photovoltaic device, said production line including at least one eye-safe analysis device having a high intensity illumination system for applying illumination with an intensity of greater than 10 Suns to the semiconductor material, and an image capture device for obtaining an image of photoluminescence emanating from said illuminated semiconductor material, said analysis device being adapted to illuminate said semiconductor material and capture an image of photoluminescence emanating from said illuminated semiconductor material without having to stop said semiconductor material as it moves through said production line.

BRIEF DESCRIPTION OF THE DRAWINGS

Benefits and advantages of the present invention will become apparent to those skilled in the art to which this invention relates from the subsequent description of exemplary embodiments and the appended claims, taken in conjunction with the accompanying drawings, in which:

DETAILED DESCRIPTION OF PREFERRED EMBODIMENTS

Preferred embodiments of the invention will now be described, by way of example only, with reference to the accompanying drawings.

Figure 3:
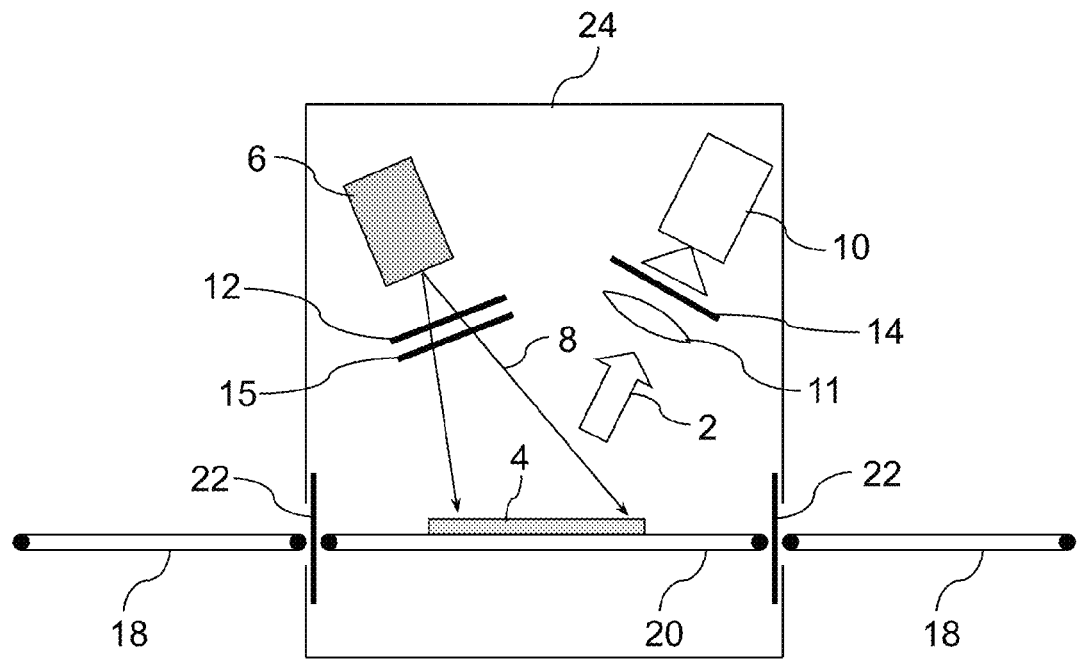
FIG. 3 illustrates a system suitable for in-line PL imaging of semiconductor samples.

FIG. 3 shows a PL imaging system according to one embodiment of the present invention, suitable for acquiring photoluminescence images of semiconductor devices during their production process without removing them from the production line. This system, hereinafter referred to as a 'three-belt system', includes two outer transport belts 18 to interface with a continuous on-belt production line or pick and place handling robots or other handling mechanism common to a production line and an inner transport belt 20 to bring the sample 4 to a stop for measurement, and optionally light-tight shutters 22 that open to allow the samples in and out of the measurement chamber 24 to satisfy light safety requirements if required, i.e. if the system would not otherwise be eye-safe. In alternative embodiments the sample is moved with some other transport mechanism such as rollers, platens or vacuum chucks rather than transport belts.

Figure 1:
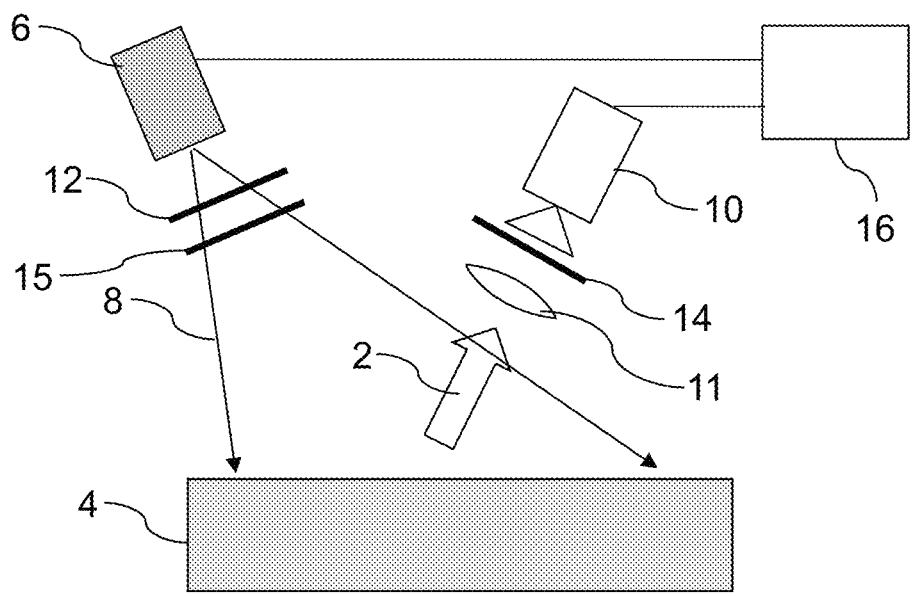
FIG. 1 illustrates a prior art system for PL imaging of a semiconductor sample.
Figure 2:
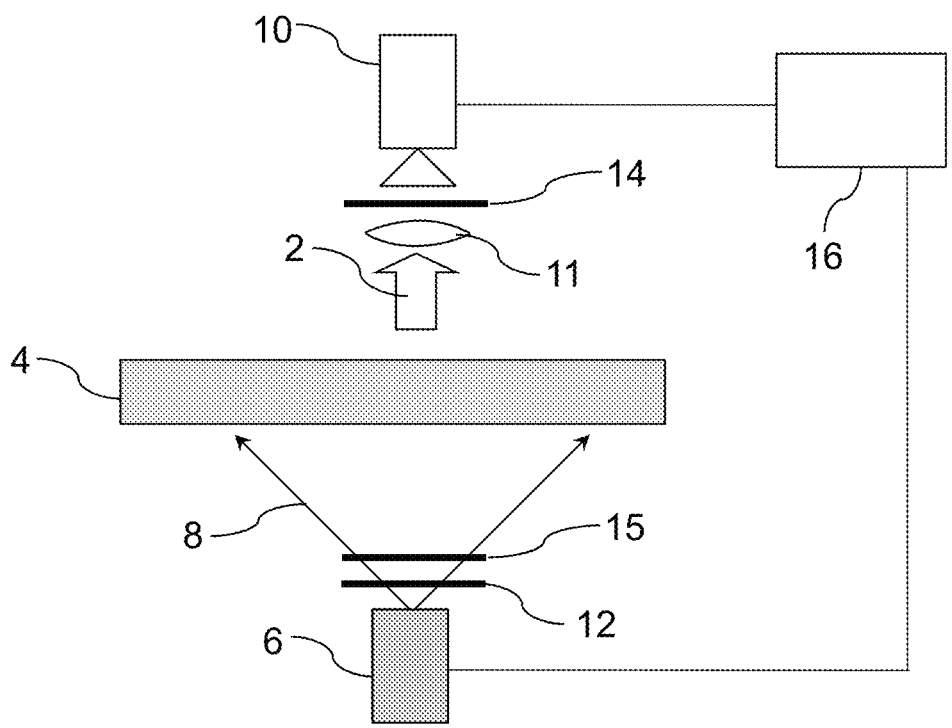
FIG. 2 illustrates another prior art system for PL imaging of a semiconductor sample.
Figure 4:
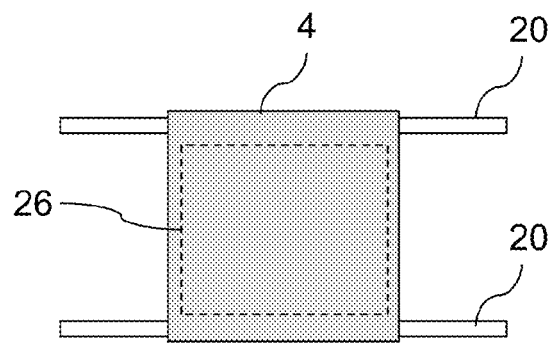
FIG. 4 shows in plan view the positioning of a semiconductor sample on a transport belt.

Although the apparatus shown in FIG. 3 has the excitation source 6 and camera 10 on the same side of the sample as in FIG. 1, the FIG. 2 arrangement is also possible because, as shown in plan view in FIG. 4, the inner transport belt 20 at least can be in split form, allowing a substantial portion 26 of the sample 4 to be illuminated and/or imaged. By way of concrete example, for a 15.6 cm×15.6 cm wafer supported on a pair of 5 mm wide transport belts, up to 93% of the wafer surface area can be available for illumination or imaging.

This three-belt system is a major advancement over the current PL imaging sampling systems, since it enables measurement of all or nearly all samples in a production process, subject to both line and tool measurement speed. In this context, it alleviates one of the major disadvantages of current PL imaging systems.

However it would be advantageous, especially with fragile wafers, or on large or fast production lines, to avoid any stop/starting of individual wafers, especially since the rate of stopping and starting becomes throughput limiting as overly rapid acceleration or de-acceleration of samples on a belt may lead to breakages or sample slip. It would be particularly advantageous to have a system that can not only measure all or most of the samples in a production process, but that does not require the sample to stop for measurement, and requires few or no light safety measures. In addition the absence of an expensive sample handling apparatus, for example using robotic pick and place sample handling utilising platens, suction cups or the like, integrated into the PL measuring system would be of economic benefit.

Specifically, it would be especially advantageous to have a PL imaging system that just included a camera, a light source and optics as the major hardware components. Such a system could be placed anywhere in a production line without requiring special modifications, for example above a transport belt bearing samples along the line. The invention is now described with reference to various systems and methods for acquiring PL images of semiconductor devices, such as fully or partially manufactured silicon solar cells, during their production process without interrupting their motion through the production line. The invention is described with reference to configurations where the imaging device and illuminator are stationary with the samples moving past them, for example, on a system of transport belts or robot grippers, however it should be noted that other configurations are also within the scope of the present invention. For example blurring can be avoided during long exposures by moving or pivoting the imaging device and/or its associated optics to follow the sample movement. In some embodiments the excitation source and/or its associated optics can also be moved or pivoted to follow the sample movement.

Before describing further embodiments of PL imaging systems, and in particular those preferred embodiments with reduced or no light safety requirements, it will be useful to include some discussion of current laser safety standards and some strategies for producing PL imaging systems with reduced light safety requirements. As mentioned previously the brightness of a source, which can be defined as the optical power passing through an aperture divided by the aperture area divided by the solid angle subtended by the optical beam in the far field, is a key parameter, and light safety issues cannot simply be ignored just because a system uses non-laser (incoherent) light sources.

In Australia and New Zealand, the standards for laser classification and safety requirements are provided by AS/NZS 2211.1:2004 and its associated guidelines (AS/NZS 2211.10: 2004), based on the international standard IEC 60825-1: 2001. An important concept in laser safety is the 'Maximum Permissible Exposure' (MPE) level, which is defined in the standard as 'that level of laser radiation to which, under normal circumstances, persons may be exposed without suffering adverse effects'. The definition further states that 'MPE levels represent the maximum level to which the eye or skin can be exposed without consequential injury immediately, or after a long time, and are related to the wavelength of the radiation, the pulse duration or exposure time, the tissue at risk and, for visible and near infra-red radiation in the range of 400 nm to 1400 nm, the size of the retinal image'.

Since the wavelengths of light suitable for generating PL from silicon are within this 400 to 1400 nm range, it follows that retinal image size is a key factor for light safety in PL imaging systems. Within certain limits, the MPE level increases with increased image size on the retina, although there is no decrease in the MPE below a certain minimum image size and no increase above a certain maximum image size. For quantitative purposes the standard uses an angular measure of the retinal image size, the angle subtended by the source at the eye, $\alpha$. This is generally referred to as the 'angular subtense' and is given approximately by the source size divided by the distance between the source and the eye. The angular subtense representing the image size below which there is no further decrease in the MPE is referred to as '$\alpha_{min}$' (1.5 mrad), and exposure conditions below this are referred to as 'point source viewing'. 'Extended source viewing' conditions apply at angular subtenses above $\alpha_{min}$, and as the angular subtense increases from $\alpha_{min}$ the MPE level increases until it reaches a maximum at $\alpha=\alpha_{max}$ (100 mrad), beyond which the MPE is constant. It is important to note that if the source radiation is modified by illumination optics, as shown in FIGS. 1-3 for example, the 'apparent source' for MPE purposes is the image, real or virtual, that produces the smallest retinal image. For the purposes of this specification, the term 'illuminator' will be used to refer to the portion of a PL imaging system that provides optical excitation to a sample. An illuminator will include one or more optical sources, possibly in combination with a number of other components including filters and focusing optics.

In the standards, laser products are classified in a system ranging from Class 1, 'safe under reasonably foreseeable conditions of operation', to Class 4, 'generally powerful enough to burn skin and cause fires', using limits known as 'accessible emission limits' (AELs). AELs are derived from MPEs using limiting apertures and may be expressed as a power limit, an energy limit, an irradiance limit, a radiant exposure limit, or a combination thereof. The limiting aperture is usually taken to be 7 mm, representing a dilated pupil as a 'worst case scenario'. Although meeting Class 1 AELs is necessary but not sufficient for making a laser product Class 1, there being other constraints, for the purposes of this specification a PL imaging system as a whole will be considered to be 'eye-safe' if it meets Class 1 AELs. Similarly, the illuminator portion of an imaging system will be considered to be 'eye-safe' if it meets Class 1 AELs.

Relatively high brightness sources, typically required for acquiring PL images of silicon PV samples on a timescale suitable for in-line applications, are potentially hazardous because they can result in a relatively high intensity at the eye, even at a distance, or a relatively small retinal image (and correspondingly low MPE level). However to determine the actual hazard, it is necessary to consider brightness in combination with the viewing conditions, in particular the angular subtense. The importance of viewing conditions is demonstrated by the following specific example. According to the calculation methodology prescribed in IEC 60825-1:2001, an 808 nm cw laser product can only be classified as Class 1 (i.e. does not exceed the Class 1 AEL) if its emission under point source viewing conditions (i.e. angular subtense $\alpha<\alpha_{min}$) does not exceed 0.64 mW through a 7 mm diameter limiting aperture. In contrast, for extended source viewing conditions where $\alpha \geq \alpha_{max}$ (100 mrad), the Class 1 AEL is 42 mW (i.e. 65× higher) through a 7 mm diameter limiting aperture.

The brightest light sources in common use are laser sources, which have high temporal coherence (or equivalently, coherence length) compared to non-laser (i.e. thermal) sources. Since coherence is an inherent aspect of the lasing process, higher coherence than thermal sources may be considered a necessary condition for achieving the highest brightness practical light sources. However coherence does not imply brightness, as it is not a sufficient condition. In general, coherence length varies widely (over orders of magnitude) between different laser types, but this does not necessarily correlate with brightness. For example the coherence length of a laser source can be increased by using a high quality factor (Q) resonator at the expense of output power, meaning that while the beam collimation (the 'per unit solid angle' part of the brightness definition) may be increased, the reduced output power reduces the 'power per unit area' part of the brightness definition, counteracting the potential increase in brightness.

Optics can be added to a light source to reduce the brightness without altering the coherence, a trivial example being an absorbing filter which may be used to reduce the brightness arbitrarily without altering the coherence. Of significant practical relevance for PL imaging systems of the present invention are illuminator designs which have reduced brightness without significantly reducing the intensity on the sample, typically all or part of a wafer or PV cell. In certain embodiments this is achieved in a second illuminator ('system 2') compared to an unimproved, prior art illuminator ('system 1') by one or both of:

(i) Increasing the solid angle filled by the light output from system 2 relative to that of system 1. This may be expressed as decreasing the 'f number' or increasing the Numerical Aperture of the illuminator, and essentially the excitation light is made to diverge more rapidly so that its intensity at a distance is reduced.

(ii) Increasing the size of the source (real or apparent, as discussed above in the context of illumination optics) in system 2, for example by dividing a single beam in system 1 into one or more beams, or an array of beamlets, in system 2, or by mechanically agitating a component of the illumination system (e.g. a mirror). If system 1 already uses a number of beamlets, their number may be significantly increased in system 2.

Approach (i) decreases the intensity of light at the eye, while approach (ii) increases the angular subtense a which, subject to the limits described above, may increase the MPE level as follows:

(a) If $\alpha$ for system 1 was greater than $\alpha_{min}$ and less than $\alpha_{max}$, then the MPE level for system 2 is greater than for system 1.

(b) If a for system 1 was less than $\alpha_{min}$ and a for system 2 is greater than $\alpha_{min}$, then the MPE level for system 2 is also greater than for system 1.

(c) If $\alpha$ for system 1 was less than $\alpha_{min}$ and $\alpha$ for system 2 is also less than $\alpha_{min}$, then the MPE level for system 2 is the same as for system 1.

By means of one or both of these measures, it is possible for an illuminator to meet Class 1 AELs (i.e. be eye-safe) even when the source itself is rated as high as Class 4. If the illuminator does not meet Class 1 AELs, with or without these measures, it is still possible for a PL imaging system as a whole, or such system integrated into a production line or other wafer/cell handling system, to meet Class 1 AELs without resorting to stringent laser safety measures such as safety shutters and interlocks. This represents a significant simplification for the system integration; for example the configuration shown in FIG. 3 would be simplified considerably if the light-tight shutters 22 were not required and the measurement chamber 24 did not have to enclose the imaging system on all sides. Instead, the PL system itself or the production line guarding may provide some minimum human access distance from the illuminator, and the PL system can prevent direct viewing of the illuminator output, i.e. viewing will be limited to reflections from a wafer or solar cell or some object in the PL system or production line. Reflections off sample edges are of particular concern, since broken wafers may present mirror-like edge surfaces at unpredictable angles. Reducing the illuminator brightness by increasing the divergence angle of the excitation light (approach (i) described above) is particularly useful in combination with measures that provide a minimum human access distance. All these details need to be considered in determining if a PL imaging system meets Class 1 AELs.

To summarise, it is preferred for a PL imaging system as a whole, or such system integrated into a production line or other wafer/cell handling system, to meet Class 1 AELs without resorting to stringent laser safety measures such as safety shutters and interlocks. More preferably, the illuminator meets Class 1 AELs. With these light safety considerations in mind, we now turn to the description of certain preferred embodiments of PL imaging systems for in-line inspection of silicon solar cell samples. For both area illumination schemes and line illumination schemes, the above described approaches can be applied to reduce light safety requirements.

In a first embodiment, referred to hereinafter as the 'flash lamp' approach and illustrated schematically in FIG. 5, a substantial area (preferably at least 1 cm×1 cm, more preferably the entirety) of a sample 4 moving through a measurement zone on a transport belt 36 is illuminated with a short pulse of excitation light 8 from one or more high intensity sources 50 such as a xenon flash lamp or a pulsed LED, and the resulting PL emission 2 from that area acquired with an area camera 10. In one specific example, a Broncola ring flash C produces a 1 millisecond pulse that, after passing through an excitation filter 15 (a 6 mm thick KG1 Schott glass short pass filter), illuminates a silicon sample with an intensity of 10-100 W/cm$^2$ (100 to 100 Suns), and an image of the PL emission acquired with a 1 Megapixel silicon CCD camera. The system may be surrounded by a cylindrical reflector 52 if greater illumination intensity on the sample is required. The system can also include collection optics 11 and a long pass filter 14 as in the FIG. 1 system, and a shroud 54 to prevent excitation light entering the camera. We note that although the overall speed of the system may be limited by the camera readout time, depending on the camera technology, this does not affect its ability to acquire PL images of moving samples with minimal blurring. In the context of the present invention this is the primary advantage of high intensity, short pulse illumination, high intensity illumination, for example up to 1000 Suns (100 W/cm$^2$) also provides surprising benefits for PL image clarity and for identifying certain defects.

Figure 5:
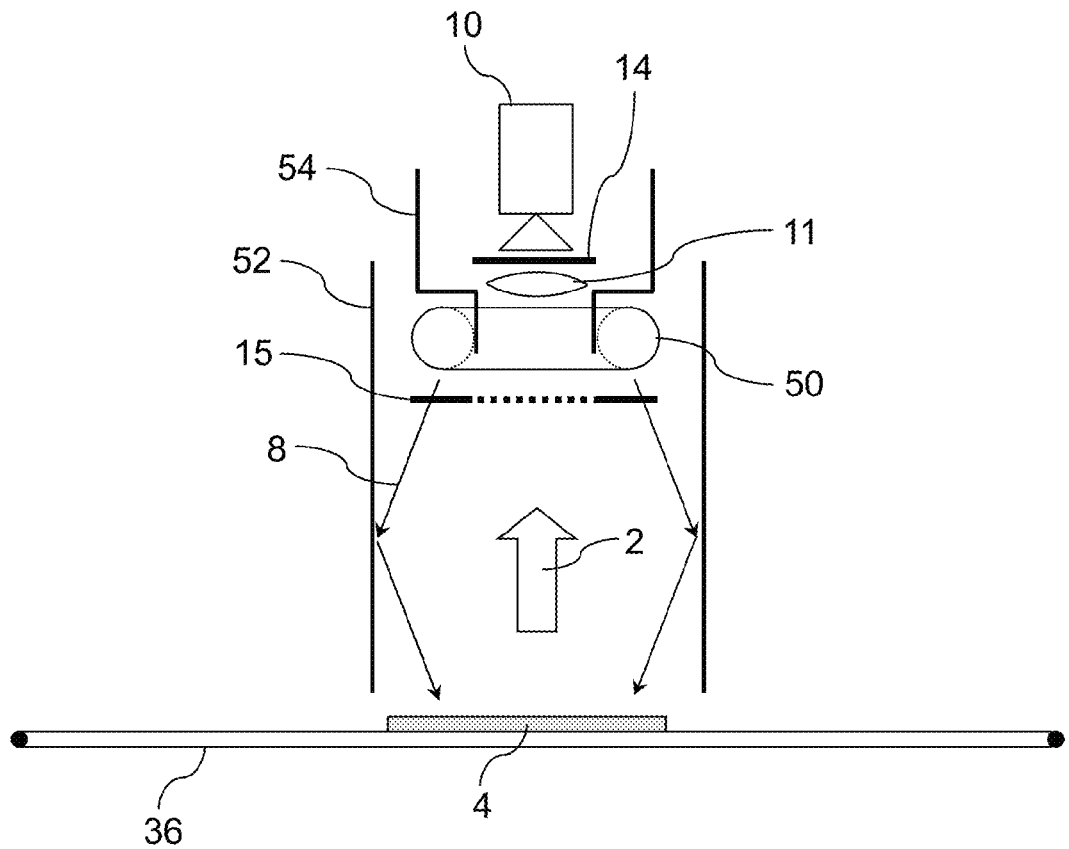
FIG. 5 illustrates in side view a PL imaging system according to an embodiment of the invention.
Figure 6:
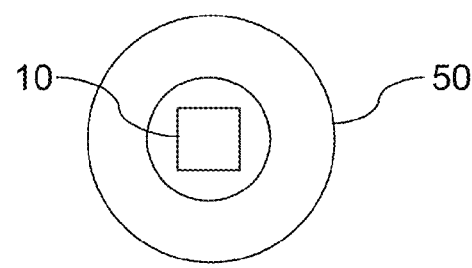
FIG. 6 shows in plan view an arrangement of a flash lamp and camera according to a preferred embodiment of the invention.

In the embodiment illustrated in FIG. 5, the flash lamp 50 is ring-shaped with the camera 10 centrally mounted, enabling both to be pointed orthogonally to the surface of a sample for greater illumination and imaging uniformity compared to configurations such as those shown in FIG. 1 where one or both of the illumination source 6 and camera 10 is angled with respect to the surface of the sample 4. This arrangement, shown schematically in plan view in FIG. 6, also has the benefit of allowing an overall more compact system and, more importantly, the camera and flash lamp can both be closer to the sample without obstructing the field of view or casting a shadow. Having the flash lamp and camera closer to the sample will generally improve the efficiency of both the illumination and PL collection systems.

Figure 7:
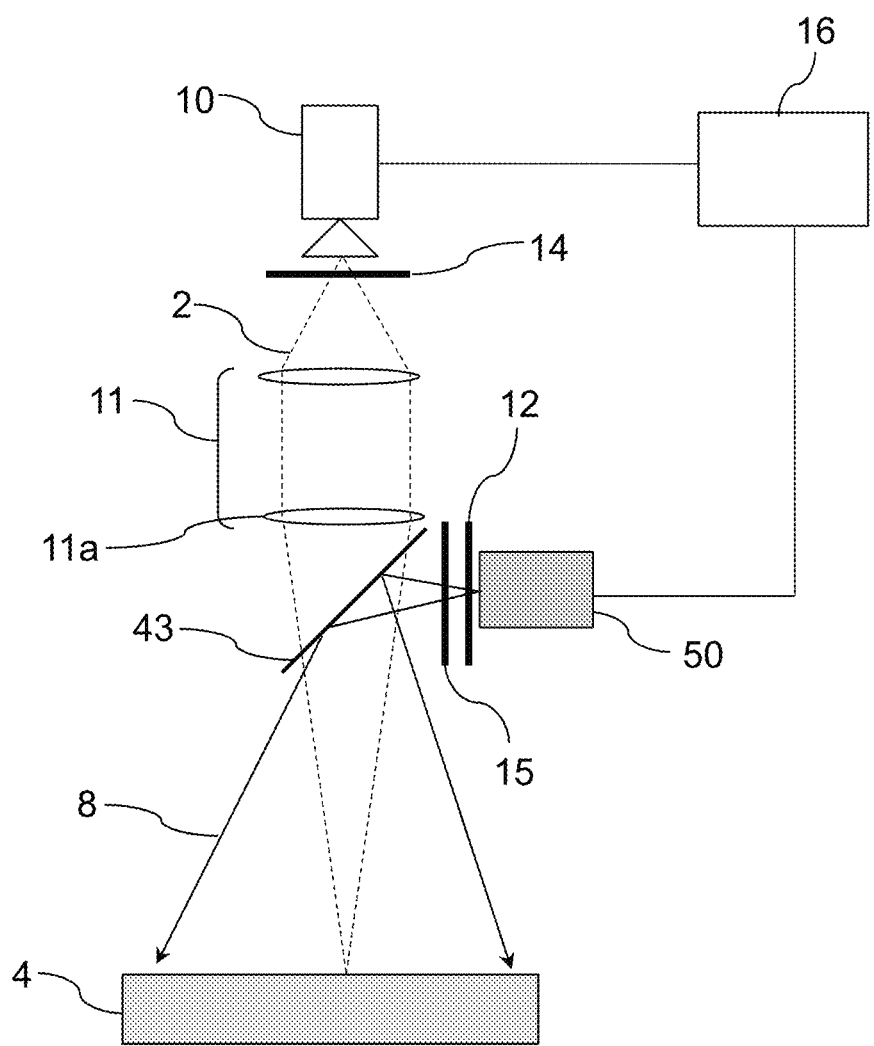
FIG. 7 shows in side view a system for PL imaging of a semiconductor sample.

In an alternative embodiment illustrated in FIG. 7, a dichroic mirror 43 is used to introduce the illumination 8 from a flash lamp 50 (or any other source of illumination suitable for generating PL) into the imaging optical system, so that the working distance can be optimised entirely for the imaging system. To mitigate the possibility of any PL generated from the dichroic mirror itself reaching the camera 10, it is preferable for the dichroic mirror to be placed well away from the sample so that the collection optics 11 do not effectively focus any such PL emission into the camera. If the system of collection optics has multiple elements as shown in FIG. 7, an advantageous position for the dichroic mirror is close to the first optical element 11a.

If the excitation light is from a broad band source such as a flash lamp, the excitation filter 15 becomes an important component because of the necessity to prevent longer wavelength excitation light (overlapping the PL emission band) from reaching the camera. Although dielectric filters have sharper transitions from high to low transmission than absorption filters, which is especially important for indirect band gap materials where the PL emission is orders of magnitude weaker than the illumination, their transmission has a strong angular dependence causing the cut-on/cut-off wavelength to vary with incidence angle. The coherent, directional emission from lasers is readily collimated for efficient filtering with dielectric filters, but this is much more difficult to achieve with the incoherent and essentially isotropic emission from flash lamps or LEDs, favouring absorption filters (such as the KG1 Schott glass filter mentioned above) or a combination of absorption and dielectric filters. We note that lamps that emit over a narrow wavelength range, such as low pressure sodium lamps that emit an extremely narrow doublet around 590 nm, may be advantageous in that the illumination can be easily separated from the silicon PL emission.

Apart from having less abrupt transitions from high to low transmission, absorption filters may also suffer from a heating problem, especially for the in-line inspection of solar cells/precursors where the flash lamp may need to be activated at a frequency of order 1 Hz or higher to inspect every sample. There are several possible ways for dealing with such a heating problem, including efficient air or liquid cooling of a solid absorption filter, and using liquid filters where an absorbing liquid is re-circulated through a flow cell, composed of glass for example, and if necessary through a heat exchanger. Solutions of organic dyes, for example a combination of the IRA 955 and IRA 1034 infrared absorbers from Exciton, Inc, may be suitable for removing excitation light in the PL emission band. UV stability of organics may be an issue when filtering flash lamp emission, but most UV light can be blocked with a judicious choice of glass flow cell material or addition of UV absorbing material in the filter or in the cooling liquid if used, and in any event the optimal solution for a given system of flash lamp, sample material and camera technology may well involve a combination of filters and cooling techniques.

In systems with flash lamp or other short pulse excitation, the image acquisition time will be determined by the overlap of the illumination time and the camera shutter time, and to minimise blurring it is generally advantageous for both to be short. In addition the illumination time (pulse duration) should be short to reduce power consumption and avoid excessive sample heating, bearing in mind that high illumination intensity is generally required to generate sufficient PL signal within a short acquisition time. Leaving the camera shutter open too long may cause image blurring if the radiative lifetime is sufficiently long for the sample to move a significant distance (e.g. by a distance corresponding to one or two camera pixels) before the PL emission has decayed, although this is only likely to be a problem for very high carrier lifetime samples such as passivated monocrystalline silicon where the lifetime can exceed several milliseconds. This effect is expected to be negligible for typical multicrystalline silicon wafers where the carrier lifetime is of order hundreds of microseconds at most.

For preference, the illumination will be provided by a pulsed excitation source with which the camera shutter is substantially synchronised. The excitation source may for example be a xenon flash lamp, a halogen flash lamp, a photographic flash, an LED or a laser, singly or in an array, with a wavelength range suitable for exciting band-to-band PL from the sample. Preferably the illuminator should be eye-safe to minimise light safety requirements. More preferably the illumination should be incoherent, i.e. the illumination source should not be a laser, although as mentioned previously incoherent illumination is not necessarily eye-safe. We note that flash lamps (and to a lesser extent LEDs) are advantageous in this regard because they are extended sources, implying that their emission cannot be focused to a point on the retina or, equivalently, limiting the minimum retinal image size. In preferred embodiments the image acquisition time is sufficiently short that the sample moves by a distance of no more than that corresponding approximately to one row of pixels in the imaging camera. This guideline depends on the speed of movement of the samples and on the number of pixel rows in the camera, but by way of example only, for a process line throughput of 1 wafer per second and a 1 megapixel camera (1024×1024 pixels), this guideline would suggest an image acquisition time of duration 1 millisecond (ms) or less, which is of order a thousand times less than the time permissible if the wafer were to be stopped for measurement. This thousand-fold decrease in acquisition time needs to be compensated by a thousand-fold increase in measurement speed, measurement speed being defined as the luminescence signal, quantified for example as counts per pixel, detected per second. It will be seen that the requisite increase in measurement speed can be provided by some combination of increased illumination intensity, improved PL collection efficiency and different camera technologies and operation.

Figure 8A:
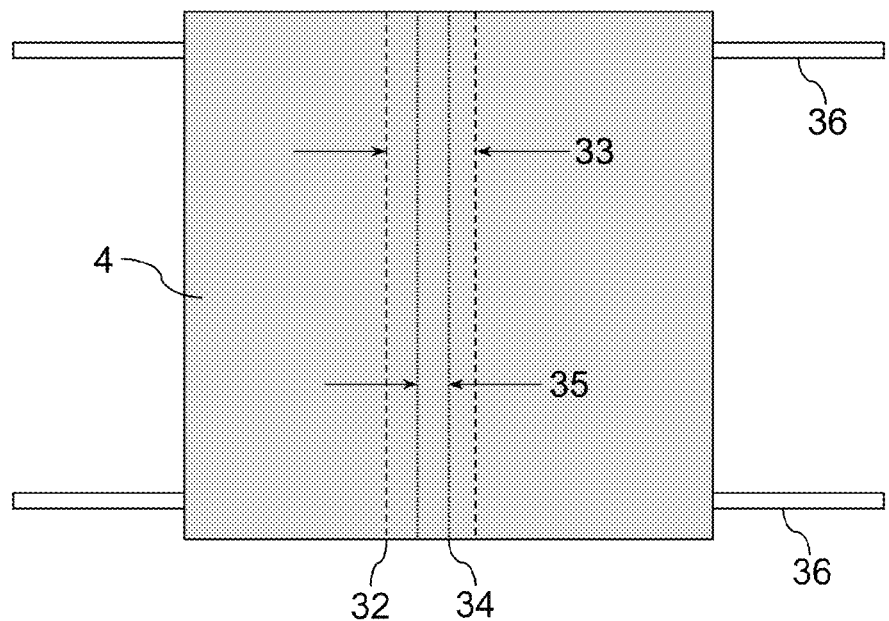
FIGS. 8A and 8B show in plan view and side view respectively a line camera system for acquiring PL images from a continuously moving sample.

In a second embodiment, referred to hereinafter as the 'line scan' approach, a line camera (e.g. silicon or indium gallium arsenide) is used instead of an area camera, and a 2-dimensional PL image acquired line-by-line as the sample passes through the measurement zone before the line camera. The illumination can be broad area but for efficiency purposes it is preferable to illuminate only the linear portion corresponding to the line camera's view, preferably with some degree of 'over-filling' of the illumination so that the illuminated and imaged areas don't have to be precisely aligned. A suitable system is shown schematically in FIGS. 8A (plan view) and 8B (side view), where the excitation source 6, line camera 28 and associated optics have been omitted from the plan view for clarity. The system includes focusing optics 30 to focus the excitation light 8 onto the sample 4 such that the illuminated portion 32 is coterminous with or slightly wider than the imaged portion 34, and collection optics 11 to image the PL emission 2 onto the line camera, as well as various other components (homogenisation optics 12, long pass filter 14, excitation filter 15 and computer 16) if required, similar to the FIG. 1 system. In this particular example the width 33 of the illuminated portion 32 is approximately three times larger than the width 35 of the imaged portion 34, corresponding to a one pixel margin either side of the imaged portion. However if the available excitation power is a limiting factor, the illuminated and imaged portions can be substantially coterminous. The sample is moved through the measurement zone on transport belts 36, from left to right in this case as indicated by the arrow 38, so that the illuminated and imaged portions are effectively scanned across the sample. The sample illumination will generally be continuous rather than pulsed, and the excitation source may for example be an array of LEDs or lasers, although for preference it is an incoherent source, i.e. not laser-based, and the illuminator as a whole is eye-safe. We note that from a light safety perspective line illumination systems can be advantageous because the eye cannot focus both axes simultaneously, limiting the minimum retinal image size. The illuminated and imaged portions need not be oriented perpendicularly to the direction of motion 38 as shown in FIG. 8A, so long as they extend across the full width of the sample or at least the full width of the sample area that needs to be measured. However a substantially perpendicular orientation minimises the area to be illuminated, thereby minimising the power requirement for the excitation source, and is therefore to be preferred.

Figure 9:
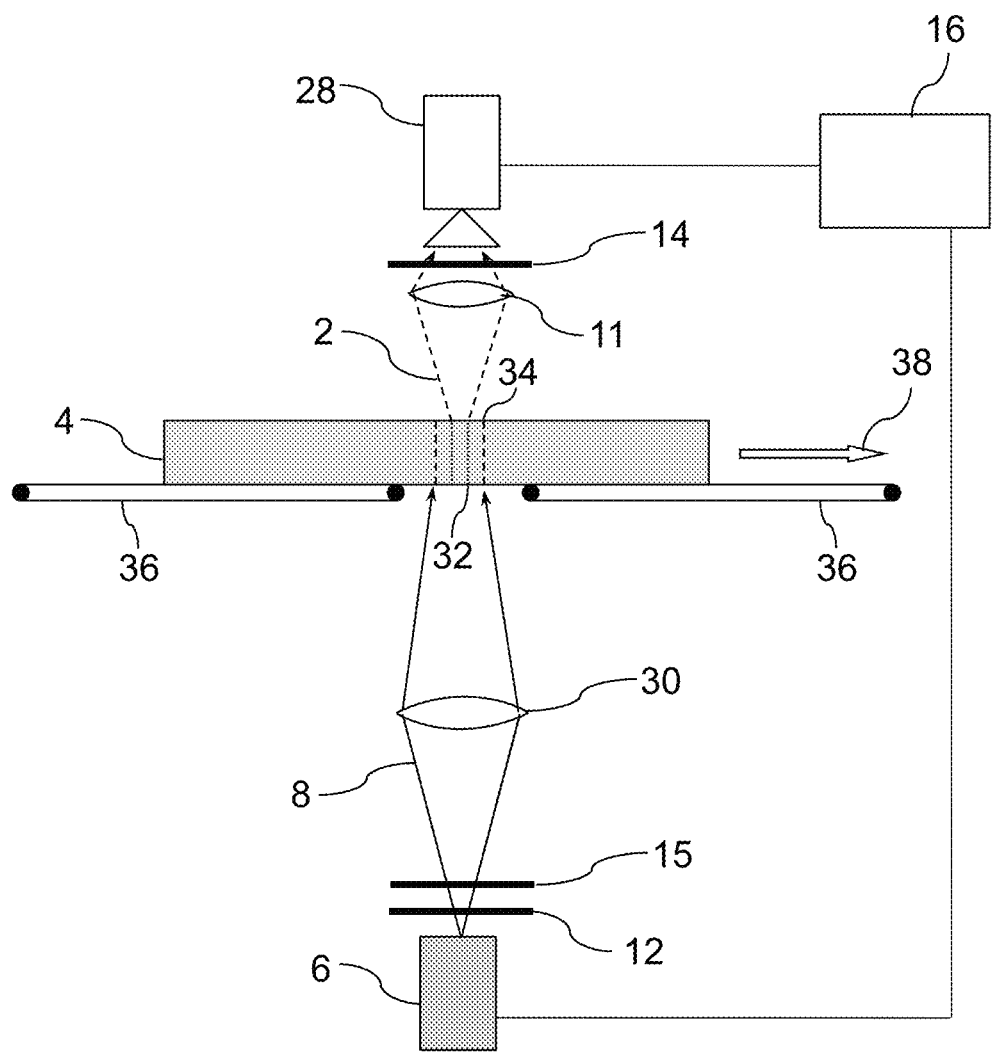
FIG. 9 shows in side view another line camera system for acquiring PL images from a continuously moving sample.

Another suitable system is shown schematically in side view in FIG. 9. In this case the transport belts 36 have a gap or unobstructed region 39 to allow the excitation source 6 and line camera 28 to be on opposite sides of the sample 4. In this particular embodiment the sample is illuminated through the gap, but in an alternative embodiment the PL emission 2 could be imaged through the gap. It will be appreciated that as a result of continued movement across the gap, the entire sample will be progressively unobstructed for illumination or imaging. In yet another alternative embodiment, suitable for samples that need not be analysed across their entire width (similar to the situation shown in FIG. 4), the gap in the transport belts is omitted.

To maximise the spatial resolution of the 'line scan' approach, the width of the imaged portion 34 should correspond to one row of pixels in the line camera 28. To achieve the same spatial resolution as would be obtained from a 1 Megapixel area camera, it is necessary to compensate for a thousand-fold decrease in PL signal acquisition time with a thousand-fold increase in measurement speed. This is essentially equivalent to the measurement speed increase for the 'flash lamp' approach described above.

Figure 10A:
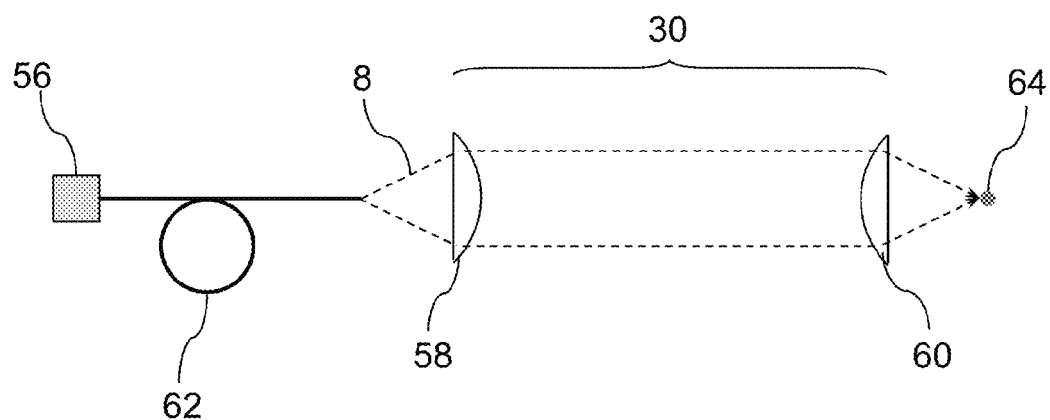
FIGS. 10A and 10B show in side view and plan view respectively an illuminator for a line camera PL system.
Figure 10B:
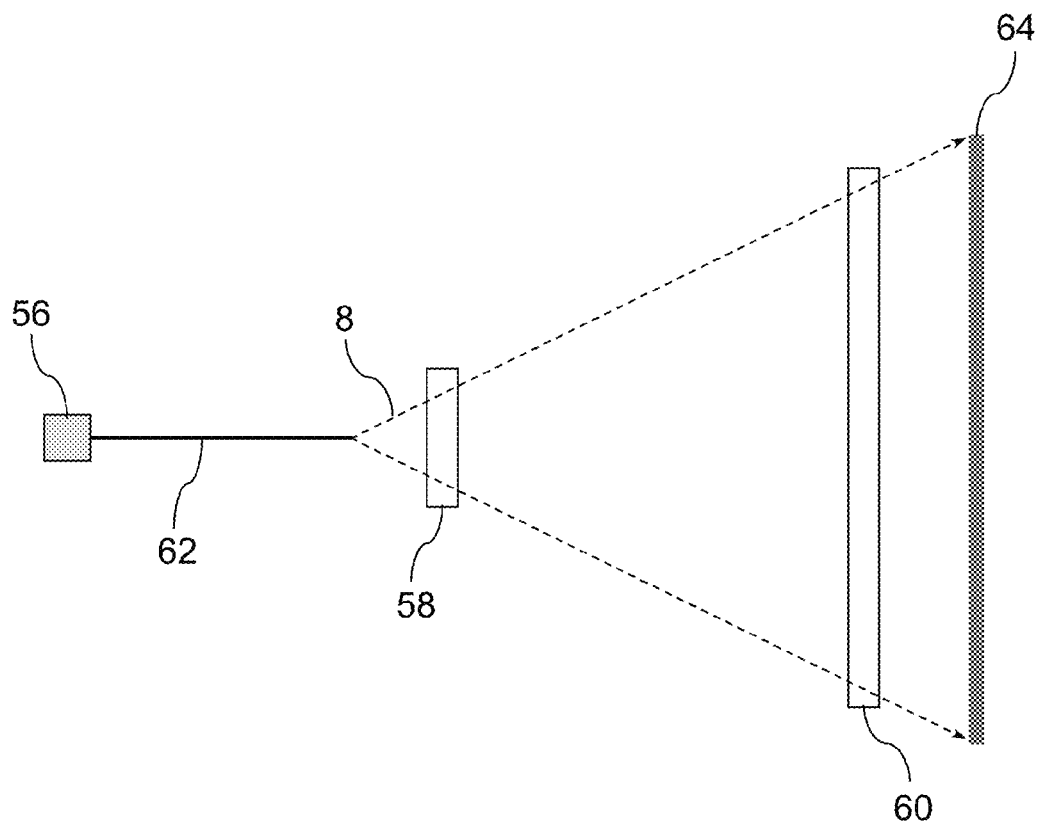

We turn now to a more detailed discussion of the illumination and imaging parts of a line scan PL imaging system. As shown in FIGS. 10A and 10B (side view and plan view respectively), a line illuminator can comprise an optical fibre coupled laser or LED array 56 and focusing optics 30 comprising a pair of cylindrical lenses 58, 60 with dimensions and focal lengths chosen according to the requirements of the specific system. As shown in FIG. 10A, excitation light 8 emerging from the optical fibre 62 is collimated in one direction by the first cylindrical lens 58, then focused to a line 64 by the second cylindrical lens 60. As shown in FIG. 10B the excitation light 8 continues to diverge in the orthogonal direction, to cover the full width of the sample. This arrangement tends to produce an approximately Gaussian intensity distribution along the line 64, determined largely by the optical fibre output, which is acceptable for PL imaging since it can be corrected with a calibration procedure, so long as the illumination intensity in the outer regions is sufficient to produce a measurable PL response. Line illuminators that produce more uniform intensity distributions are also known in the art.

Figure 11A:
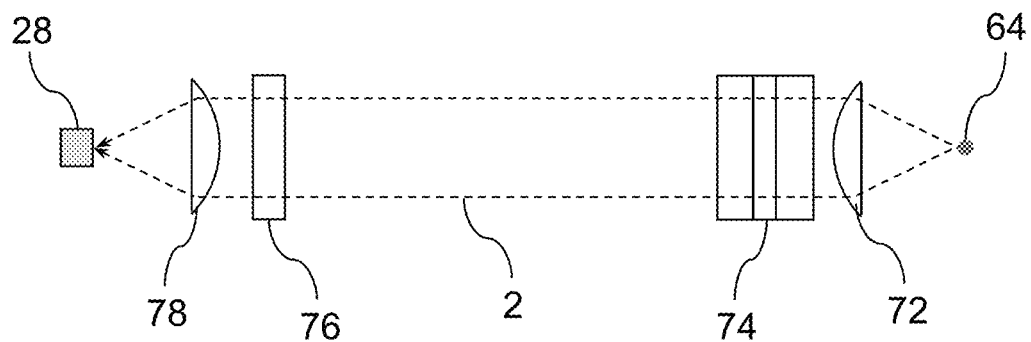
FIGS. 11A and 11B show in side view and plan view respectively a system of collection optics for a line camera PL system.
Figure 12:
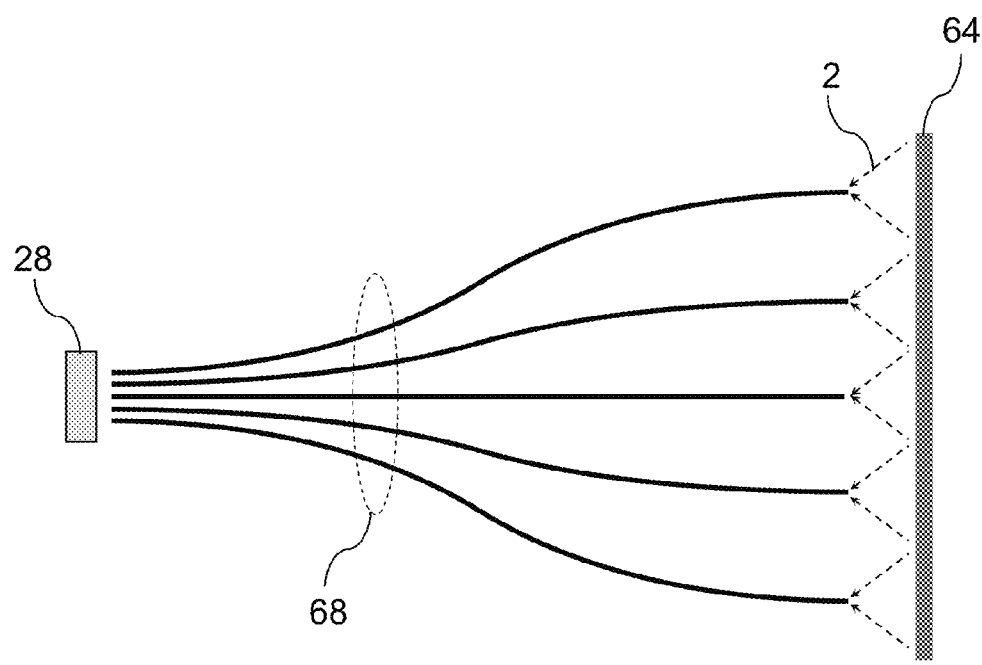
FIG. 12 shows another system of collection optics for a line camera PL system.

Turning now to consideration of collection optics, one possible system, comprising an arrangement of four cylindrical lenses with dimensions and focal lengths chosen according to specific apparatus requirements, is illustrated in FIGS. 11A (side view) and 11B (plan view). PL emission 2 from the illuminated line 64 is collimated in one direction with a first cylindrical lens 72, demagnified with a pair of cylindrical lenses 74, 76 in a 'beam expander' configuration, and focused onto the line camera 28 with a fourth cylindrical lens 78. A number of other possible systems of collection optics with varying degrees of complexity will occur to those skilled in the art, using components such as lenses, mirrors and optical waveguides. For example FIG. 12 illustrates schematically a system where an array 68 of widely spaced optical fibres collects PL emission 2 from an illumination line 64, optionally with the aid of lenses, and guides it to a line camera 28. Generally speaking the choice will be informed by factors such as cost (with off-the-shelf optical components preferred over custom-made components) and the required collection efficiency; for example if the PL signal is relatively strong, or if a high sensitivity camera is used, a standard camera lens may suffice.

Figure 8B:
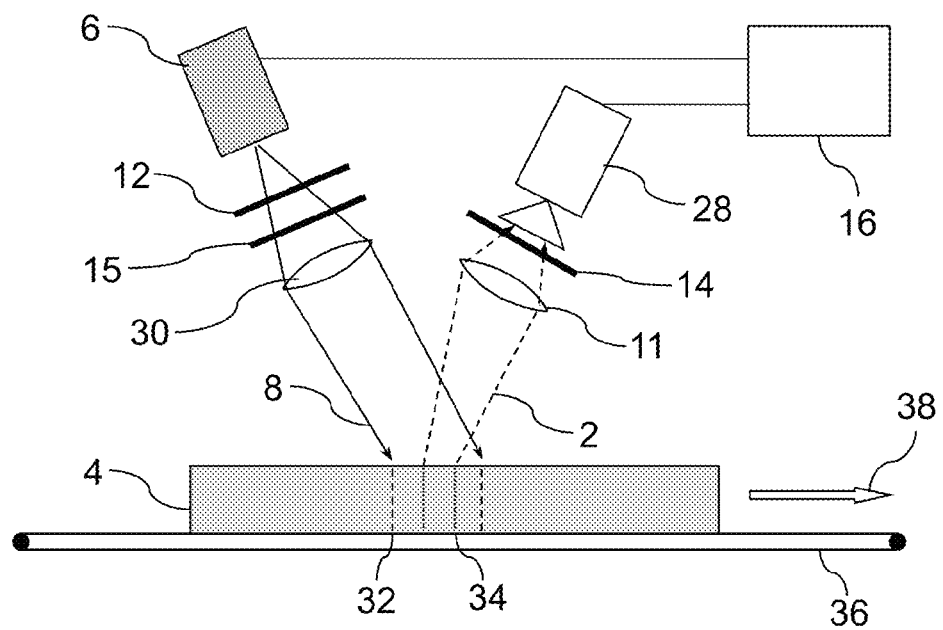
Figure 11B:
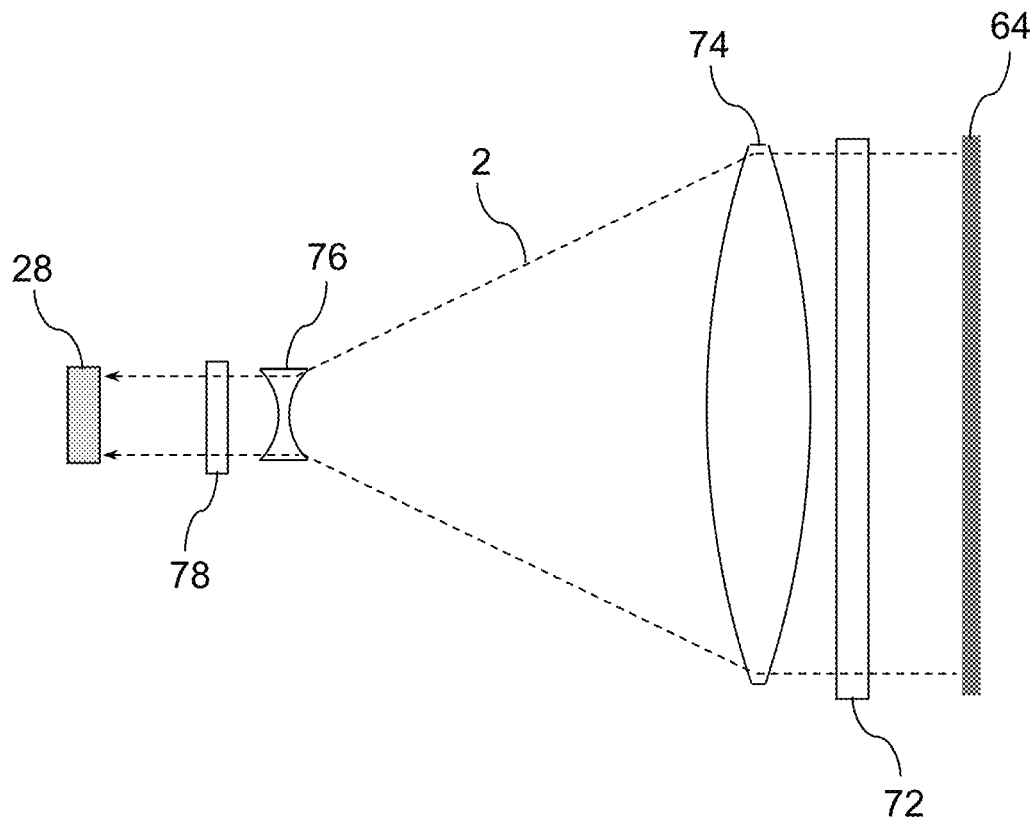

An important difference between 'line scan' imaging (illustrated in FIGS. 8A, 8B and 9) and the more conventional area imaging (illustrated in FIGS. 1 and 5 for example) is that the light gathering portion of the collection optics (lenses 72 and 74 in FIGS. 11A and 11B) can be located quite close to the sample without obscuring the illumination, greatly enhancing the collection efficiency (which may be defined as the number (or rate) of luminescence photons that are detected divided by the number (or rate) of luminescence photons emitted by the sample into a hemisphere). Depending on the design details, we estimate that the collection optics shown in FIGS. 11A and 11B are two or three orders of magnitude more efficient than the typical collection optics of a conventional 'area imaging' (FIG. 1) PL system, quantified below in the 'baseline example'.

Similarly, the illuminator can be located quite close to the sample without obscuring the PL collection optics, which can be advantageous for light safety. To explain with reference to FIG. 10B, the closer the illuminator is to the sample, the greater the divergence of the excitation light 8 impinging on the sample, reducing the brightness of the illuminator.

Under quasi steady state conditions, a reasonable approximation even for millisecond-level illumination times as may be used with a flash-lamp for example since the minority carrier lifetime in silicon as used in the solar industry is typically of order 10 to 100 μs, the minority carrier concentration Δn (which affects the PL intensity) and the generation rate G (determined by the illumination intensity among other things) are related by the equation Δn=G*τ where τ is the minority carrier lifetime. From this it follows that, for a given illumination intensity, a stronger PL signal will be obtained from a sample with a longer carrier lifetime, e.g. monocrystalline silicon compared to multicrystalline silicon, or a passivated silicon wafer (in later stages of a solar cell line) compared to a raw silicon wafer. Although the minority carrier lifetime τ can only be considered to be constant at low injection levels (i.e. low Δn), in general a stronger PL signal will also result from more intense illumination, i.e. larger generation rate G, which is an important aspect of the 'flash lamp' approach described previously.

As described in PCT patent application No AU2010/001045 entitled 'Photoluminescence imaging systems for silicon photovoltaic cell manufacturing', incorporated herein by reference, it is sometimes preferable when performing PL imaging of silicon samples to use a camera technology such as indium gallium arsenide (InGaAs) that, unlike silicon-based cameras, is sensitive across the entire silicon PL emission spectrum. All other things being equal, we estimate that replacing a silicon camera with an InGaAs camera improves measurement speed by some 20×. Measurement speed can also be improved by using cameras with larger pixels or, at the expense of spatial resolution, binning pixels.

Figure 13:
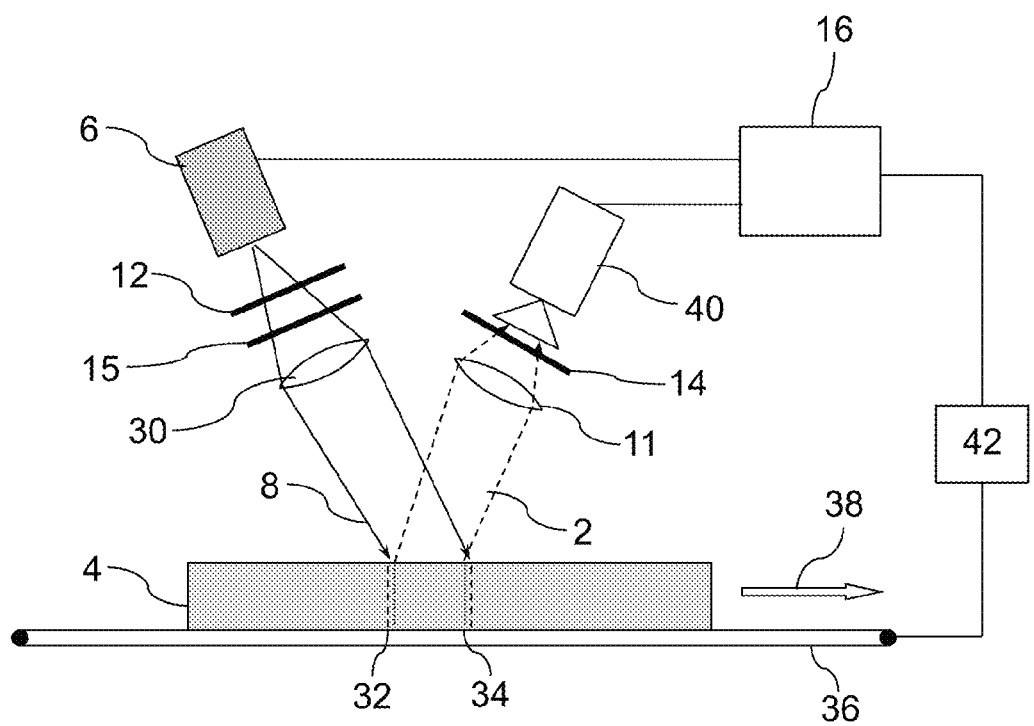
FIG. 13 shows in side view a TDI camera system for acquiring PL images from a continuously moving sample.

A third embodiment, somewhat similar to the 'line scan' approach, uses a time delay integration (TDI) camera. A TDI camera can be thought of as an integrated array of line cameras, e.g. 96 or 128 lines of 1024 pixels on a single chip, typically using the same silicon CCD technology as in conventional line or area cameras. TDI cameras are well suited for acquiring images of a moving sample, with the direction of movement perpendicular to the pixel lines: as the sample is moved, the charge from the detected signal is transferred to the next pixel line and accumulated, with synchronisation of the transport speed and the charge transfer. Consequently, a TDI camera with N pixel lines measures the signal from a given portion of a sample N times, improving the signal-to-noise ratio by a factor of √N compared to a line camera for the same total measurement time. A suitable system for this 'TDI camera' approach is shown schematically in side view in FIG. 13, and it will be seen that the configuration is quite similar to the line scan system shown in FIG. 8B but with a TDI camera 40 in place of the line camera. FIG. 13 also shows a transport belt drive unit 42 controlled by the computer 16, in accordance with the need to synchronise the motion of the sample 4 with the TDI camera operation. A significant but less obvious difference with the line scan system is that for a TDI camera with N pixel lines, the imaged portion 34 needs to be N times wider than for the line scan system. With a one pixel margin either side of the imaged portion as for the 'line scan' configuration shown in FIGS. 8A and 8B, the illuminated portion 32 will be a factor of (N+2)/3 wider than in the line scan configuration; alternatively the illuminated portion will be N times wider than in the line scan configuration if the illuminated and imaged portions are coterminous. Either way, for a given excitation source 6 the illumination intensity on the sample will be reduced by the same factor, and when designing a TDI system this needs to be considered against the N times longer signal acquisition time advantageously provided by the N pixel lines. Finally, it will be appreciated that the variant configurations discussed above for line camera systems, e.g. the configuration shown in FIG. 9, are also applicable to TDI systems.

EXAMPLES

In this section a 'baseline example' of an optical system is provided, such as may be found in a prior art PL imaging system with full field imaging onto an area camera, illustrated schematically for example in FIG. 1 or 2, with which all subsequent examples are to be compared. It is assumed that measurement noise is dominated by statistical noise, i.e. the signal to noise is given as the square root of the total number of counts, and define 2000 counts per pixel as the target for PL measurements that have sufficient signal to noise. Several measurement parameter/sample/hardware combinations will be outlined that yield this target, and it will be observed that there are general rules that can be used to derive alternative combinations. In each case the sample will be a 156 mm×156 mm, 200 μm thick 1 Ω·cm p-type silicon wafer, but the specific material quality will vary between three possibilities:

As-cut unpassivated multicrystalline silicon, with an effective carrier lifetime of 0.5 to 2 μs ('worst case')

Passivated or diffused multicrystalline silicon, with an effective carrier lifetime of around 10 μs High lifetime passivated monocrystalline silicon, with an effective carrier lifetime of around 1 ms ('best case')

Baseline Example

Referring to FIG. 1, a 156×156 mm$^2$ sample 4 is illuminated with 750 nm light at an on-sample intensity of 100 mW/cm$^2$ (1 Sun), and the photoluminescence 2 focused onto a Si CCD-based 1 Megapixel (1024×1024 pixels) camera 10 having 5×5 μm$^2$ pixels using collection optics 11 comprising an F#=2.8 lens with a focal length f=25 mm. To estimate the collection efficiency, it is noted that to focus the entire sample area onto the camera chip, the collection optics needs to have a magnification M=1024×5e-3/156=0.033, requiring an object distance (i.e. the distance between the lens and the sample) of O=(1+1/M)*f=787 mm. Noting that the aperture of the lens is given by D=f/F#=25 mm/2.8=8.9 mm, the acceptance area of the lens will be $\pi D^2/4$=63 mm$^2$. Comparing this with the surface area of a hemisphere of radius O ($2\pi O^2$), a collection efficiency of 0.0016% is calculated.

With this system, it is estimated that an unpassivated multicrystalline silicon sample will yield between 2 and 6 counts per second per pixel, implying a total measurement time of between 330 and 1000 s to achieve 2000 counts. In comparison, because of the longer carrier lifetime an estimated 2000 counts could be achieved in about 60 s or 600 ms for passivated multicrystalline silicon or high lifetime passivated silicon samples respectively.

Example 1

2D area imaging geometry in three-belt system of FIG. 3 (stationary sample).

To incorporate a three-belt system into a solar cell line with a throughput of one cell per second, the measurement time clearly cannot exceed one second. To guarantee this for unpassivated samples it is necessary to achieve a thousand-fold increase in measurement speed. This could be done for example with a combination of:
1) Si-CCD camera with 20×20 µm$^2$ pixels (16× gain compared to the baseline example)
2) F#=2 lens (2× gain)
3) Illumination intensity of 1 W/cm$^2$ i.e. 10 Suns (10× gain)
4) 2×2 pixel binning (4× gain)

It will be appreciated that many other combinations are possible, e.g. 40 Suns illumination without pixel binning

Example 2

Line scan system with Line illumination (165 µm width and 156 mm length) and detection on unpassivated wafer.

In this case a 1 ms measurement time per line is needed, requiring a 10$^6$ times increase in measurement speed compared to the Baseline Example. One possible combination is:
1) InGaAs camera (20× gain)
2) 25×25 µm$^2$ pixels (25× gain)
3) Illumination intensity of 1 W/cm$^2$ i.e. 10 Suns (10× gain)
4) Improved collection efficiency (200× gain)

It should be noted that because the illuminated area is much smaller than in the Baseline Example, it would be relatively straightforward to use much higher illumination intensities (hundreds of Suns) if collection efficiency improvements are more limited.

Example 3

Line scan system with line (165 µm width and 156 mm length) illumination and detection on passivated multicrystalline wafer.

As for Example 2 a 1 ms measurement time per line is needed, which in this case requires a 60,000 times increase in measurement speed compared to the Baseline Example. One possible combination is:
1) Si-CCD camera with 20×20 µm$^2$ pixels (16× gain)
2) Illumination intensity of 2 W/cm$^2$ i.e. 20 Suns (20× gain)
3) Improved collection efficiency (200× gain)

Alternatively an InGaAs camera would give the required measurement speed if collection efficiency improvements are more limited, or if the PL intensity increases sub-linearly with illumination intensity.

Example 4

Line scan system with line (165 µm width and 156 mm length) illumination and detection on high lifetime passivated wafer.

In this case a 600 times increase in measurement speed is required to achieve a 1 ms measurement time. One possible combination is:
1) Si-CCD camera with 20×20 µm$^2$ pixels (16× gain)
2) Illumination intensity of 0.2 W/cm$^2$ i.e. 2 Suns (2× gain)
3) Improved collection efficiency (20× gain)

The increase in measurement speed could alternatively be achieved with the baseline geometry, i.e. without any modification of the imaging system to improve the collection efficiency, if an illumination intensity of 40 Suns were used.

Example 5

Flash based system with broad illumination spectrum (500-800 nm) on unpassivated wafer.

A 1 ms measurement time is needed, i.e. a 10$^6$ times improvement compared to the Baseline Example. Assuming that the response of an unpassivated wafer to that spectrum is on average the same as for 750 nm excitation, one possible combination is:
1) InGaAs camera (20× gain)
2) 25×25 µm$^2$ pixels (25× gain)
3) Illumination intensity of 50 W/cm$^2$ i.e. 500 Suns (500× gain)
4) F#=1.4 lens or 2×2 pixel binning (4× gain)

It will be noted that an extremely high illumination intensity is used.

Example 6

Flash based system with broad illumination spectrum (500-800 nm) on passivated multicrystalline wafer.

A 1 ms measurement time is needed, i.e. a 60,000 times improvement compared to the Baseline Example. One possible combination is:
1) Si-CCD camera with 20×20 µm$^2$ pixels (16× gain)
2) Illumination intensity of 10 W/cm$^2$ i.e. 100 Suns (100× gain)
3) F#=1.4 lens (4× gain)
4) 3×3 pixel binning (9× gain)

Using an InGaAs camera or improved collection efficiency would allow lower illumination intensities; these options would also be useful if the PL intensity increases sub-linearly with illumination intensity.

Example 7

Flash based system with broad illumination spectrum (500-800 nm) on high lifetime passivated wafer.

A 1 ms measurement time is needed, i.e. a 600 times improvement compared to the Baseline Example. One possible combination is:
1) Si-CCD camera with 20×20 µm$^2$ pixels (16× gain)
2) Illumination intensity of 2 W/cm$^2$ i.e. 20 Suns (20× gain)
3) F#=2 lens (2× gain)

This can be achieved with the baseline geometry, i.e. without any modification of the imaging system to improve the collection efficiency.

Example 8

TDI camera system with 128 lines on unpassivated wafer.

2000 counts per pixel is needed with 128 ms exposure time for each part of the wafer, implying an 8000 times improvement in measurement speed compared to the Baseline Example. One possible combination is
1) Si-CCD camera with 20×20 µm$^2$ pixels (16× gain)
2) Illumination intensity of 1 W/cm$^2$ i.e. 10 Suns (10× gain)
3) Improved collection efficiency (50× gain)

Alternatively an InGaAs camera can provide the required measurement speed if collection efficiency improvements are more limited.

Example 9

TDI camera system with 128 Lines on passivated multicrystalline wafer.

2000 counts per pixel are needed with 128 ms exposure time for each part of the wafer, implying a 400 times improvement compared to the Baseline Example. One possible combination is:

1) Si-CCD camera with 20×20 μm$^2$ pixels (16× gain)
2) Illumination intensity of 1 W/cm$^2$ i.e. 10 Suns (10× gain)
3) 2×2 pixel binning (4× gain)

Example 10

TDI camera system with 128 lines on high lifetime passivated wafer.

2000 counts per pixel are needed with 128 ms exposure time for each part of the wafer, implying a 4 times improvement compared to the Baseline Example. This can be achieved simply by using 4 times the illumination intensity or 2×2 pixel binning In the above-described preferred embodiments, semiconductor samples have been subjected to a photoluminescence analysis in the form of PL imaging, i.e. the acquisition of a 2-dimensional image of the photoluminescence generated from a substantial area of each sample, with a view to deriving spatially resolved information on one or more material properties. However other forms of photoluminescence analysis are also within the scope of the present invention. For example the PL emission from the illuminated area could be fed into a spectrometer to analyse the spectral content, say to look for a PL band indicative of an impurity. In another example the total PL emission signal could be measured to yield information on the average value of a sample property, with the averaging being performed line-by-line or across the entire illuminated area, or to provide a rapid method for identifying defective (e.g. shunted) solar cells during or after manufacture.

Although the present invention has been described with particular reference to certain preferred embodiments thereof, variations and modifications of the present invention can be effected within the spirit and scope of the following claims.

The claims defining the invention are as follows:

1. A method for analyzing a sample of a semiconductor material, said method comprising the steps of:
    passing said sample to a measurement zone;
    applying an illumination to said sample to produce a photoluminescence response from said semiconductor material; and
    conducting at least a photoluminescence analysis of said sample in said measurement zone while maintaining motion of said sample,
    wherein said photoluminescence analysis comprises providing a multi-pixel image capture device for acquiring an image of the photoluminescence emitted from said sample,
    wherein said illumination is provided by a source positioned so as to illuminate a first portion of said sample, and said image capture device is positioned so as to detect photoluminescence emitted from a second portion of said sample, wherein said first portion and said second portion are at least partially overlapping, and
    said method further comprises the steps of:
    moving said sample relative to said source and to said image capture device such that said second portion is scanned across a substantial area of said sample; and
    interrogating said image capture device repeatedly to acquire an image of the photoluminescence emitted from said area,
    wherein said image capture device comprises a line camera or a time delay integration camera, and
    said first portion is from one to five times wider than said second portion in the direction of movement of said sample.

2. A method according to claim 1, wherein said illumination is provided by a non-laser source.

3. A method according to claim 1, wherein said illumination is provided by an eye-safe illuminator.

4. A method according to claim 1, wherein said first and second portions extend across a substantial fraction of a dimension of said sample, said dimension being substantially perpendicular to the direction of movement of said sample.

5. A method according to claim 1, wherein said method is applied to a sample of a semiconductor material comprising raw or unpassivated silicon.

6. A method according to claim 5, wherein said photoluminescence is generated with an illumination intensity between about 1 and 100 W/cm$^2$.

7. A method according to claim 1, wherein said method is applied to a sample of a semiconductor material comprising passivated silicon.

8. A method according to claim 7, wherein said photoluminescence is generated with an illumination intensity between about 0.1 and 10 W/cm$^2$.

9. A method according to claim 1 wherein the illumination source, the image capture device or an optical element associated with the illumination source or the image capture device moves within the measurement zone.

10. A method according to claim 9 wherein motion of the illumination source, the image capture device or an optical element associated with the illumination source or the image capture device is controlled to maintain a predetermined alignment with the sample.

11. A method according to claim 1, wherein said analysis is performed in less than 1 second.

12. A system for conducting an analysis of a sample of a semiconductor material, comprising:
    a transport mechanism configured to transport said sample to a measurement zone;
    analysis equipment configured to conduct at least a photoluminescence analysis of said sample within said measurement zone, said analysis equipment comprising a source of predetermined illumination suitable for generating photoluminescence from said semiconductor material, and a multi-pixel image capture device for acquiring an image of the photoluminescence emitted from said sample; and
    a motion apparatus configured to maintain motion of said sample within said measurement zone during said analysis
    wherein said source is configured to illuminate a first portion of said sample, and said image capture device is configured to detect photoluminescence emitted from a second portion of said sample, wherein said first portion and said second portion are at least partially overlapping, and
    wherein said analysis equipment further comprises an interrogation module configured to interrogate said image capture device repeatedly while said motion apparatus moves said sample such that said second portion is scanned across a substantial area of said sample, to acquire an image of the photoluminescence emitted from said substantial area,
wherein said image capture device comprises a line camera or a time-delay integration camera, and
said first portion is from one to five times wider than said second portion in the direction of movement of said sample.

13. A system according to claim 12 wherein the illumination source, the image capture device or an optical element associated with the illumination source or image capture device is capable of moving within the measurement zone.

14. A system according to claim 13 wherein motion of the illumination source, the image capture device or an optical element associated with the illumination source or image capture device therewith is controllable to maintain a predetermined alignment with a sample.

15. A system according to claim 12, wherein said measurement zone comprises a shuttered or enclosed chamber.

16. A system according to claim 12, wherein said measurement zone is eye-safe without being enclosed.

17. A system according to claim 16, wherein said source comprises an eye-safe illuminator.

18. A method for analyzing a sample of a semiconductor material, said method comprising the steps of:
passing said sample to a measurement zone;
applying an illumination to said sample to produce a photoluminescence response from said semiconductor material; and
conducting at least a photoluminescence analysis of said sample in said measurement zone while maintaining motion of said sample,
wherein said photoluminescence analysis comprises the steps of acquiring an image of the photoluminescence emitted from said sample with a multi-pixel image capture device,
wherein said method is applied to a sample of a semiconductor material comprising raw or unpassivated silicon, and
wherein said photoluminescence is generated with an illumination intensity between about 1 and 100 W/cm$^2$.

19. A method according to claim 18, wherein said illumination is applied to an area of said sample and said image is acquired with an area image capture device in an acquisition time t, and
wherein said sample is moving at a speed v relative to said area image capture device, and wherein the product of the acquisition time t (s) and the speed v (m/s) is less than a distance on said sample corresponding to one row of pixels in said area image capture device.

20. A method according to claim 19, wherein said illumination is provided by a non-laser source.

21. A method according to claim 19, wherein said illumination is provided by an eye-safe illuminator.

22. A method according to claim 19, wherein said illumination comprises a pulse of light.

23. A method according to claim 18, wherein said illumination is provided by a source positioned so as to illuminate a first portion of said sample and said image capture device is positioned so as to detect photoluminescence emitted from a second portion of said sample,
wherein said first portion and said second portion are at least partially overlapping, and wherein said method further comprises the steps of:

moving said sample relative to said source and to said image capture device such that said second portion is scanned across a substantial area of said sample; and
interrogating said image capture device repeatedly to acquire an image of the photoluminescence emitted from said area.

24. A method according to claim 23, wherein said illumination is provided by a non-laser source.

25. A method according to claim 23, wherein said illumination is provided by an eye-safe illuminator.

26. A method according to claim 23, wherein said image capture device comprises a line camera or a time-delay integration camera.

27. A method according to claim 23, wherein said first portion is substantially coterminous with said second portion.

28. A method according to claim 23, wherein said first and second portions extend across a substantial fraction of a dimension of said sample, said dimension being substantially perpendicular to the direction of movement of said sample.

29. A method according to claim 23, wherein the illumination source, the image capture device or an optical element associated with the illumination source or the image capture device moves within the measurement zone.

30. A method according to claim 29, wherein motion of the illumination source, the image capture device or an optical element associated with the illumination source or the image capture device is controlled to maintain a predetermined alignment with the sample.

31. A method according to claim 18, wherein said analysis is performed in less than 1 second.

32. A method for analyzing a sample of a semiconductor material, said method comprising the steps of:
passing said sample to a measurement zone;
applying an illumination to said sample to produce a photoluminescence response from said semiconductor material; and
conducting at least a photoluminescence analysis of said sample in said measurement zone while maintaining motion of said sample,
wherein said photoluminescence analysis comprises the steps of acquiring an image of photoluminescence emitted from said sample with a multi-pixel image capture device,
wherein said method is applied to a sample of a semiconductor material comprising passivated silicon, and
said photoluminescence is generated with an illumination intensity between about 0.1 and 10 W/cm$^2$.

33. A method according to claim 32, wherein said illumination is applied to an area of said sample and said image is acquired with an area image capture device in an acquisition time t,
wherein said sample is moving at a speed v relative to said area image capture device, and
wherein the product of the acquisition time t (s) and the speed v (m/s) is less than a distance on said sample corresponding to one row of pixels in said area image capture device.

34. A method according to claim 33, wherein said illumination is provided by a non-laser source.

35. A method according to claim 33, wherein said illumination is provided by an eye-safe illuminator.

36. A method according to claim 33, wherein said illumination comprises a pulse of light.

37. A method according to claim 32, wherein said illumination is provided by a source positioned so as to illuminate a first portion of said sample and said image capture device is positioned so as to detect photoluminescence emitted from a second portion of said sample,
wherein said first portion and said second portion are at least partially overlapping, and
wherein said method further comprises the steps of:
moving said sample relative to said source and to said image capture device such that said second portion is scanned across a substantial area of said sample; and
interrogating said image capture device repeatedly to acquire an image of the photoluminescence emitted from said area.

38. A method according to claim 37, wherein said illumination is provided by a non-laser source.

39. A method according to claim 37, wherein said illumination is provided by an eye-safe illuminator.

40. A method according to claim 37, wherein said image capture device comprises a line camera or a time-delay integration camera.

41. A method according to claim 37, wherein said first portion is substantially coterminous with said second portion.

42. A method according to claim 37, wherein said first and second portions extend across a substantial fraction of a dimension of said sample, said dimension being substantially perpendicular to the direction of movement of said sample.

43. A method according to claim 37, wherein the illumination source, the image capture device or an optical element associated with the illumination source or the image capture device moves within the measurement zone.

44. A method according to claim 43, wherein motion of the illumination source, the image capture device or an optical element associated with the illumination source or the image capture device is controlled to maintain a predetermined alignment with the sample.

45. A method according to claim 32, wherein said analysis is performed in less than 1 second.

46. A system for conducting an analysis of a sample of a semiconductor material, comprising:
a transport mechanism configured to transport said sample to a measurement zone;
analysis equipment configured to conduct at least a photoluminescence analysis of said sample within said measurement zone, said analysis equipment comprising a source of predetermined illumination suitable for generating photoluminescence from said semiconductor material, and a multi-pixel image capture device for acquiring an image of the photoluminescence emitted from said sample; and
a motion apparatus configured to maintain motion of said sample within said measurement zone during said analysis,
wherein said system is configured to conduct an analysis of a sample of a semiconductor material comprising raw or unpassivated silicon, and said source is configured to generate photoluminescence with an illumination intensity between about 1 and 100 W/cm$^2$.

47. A system according to claim 46, wherein said source of predetermined illumination is adapted to illuminate an area of said sample, and said image capture device is an area image capture device adapted to capture an image of said photoluminescence in an image acquisition time t,
wherein said motion apparatus is adapted to move said sample at a speed v relative to said area image capture device such that the product of the image acquisition time t (s) and the speed v (m/s) is less than a distance on said sample corresponding to one row of pixels in said area image capture device.

48. A system according to claim 47, wherein said source is adapted to provide illumination comprising a pulse of light.

49. A system according to claim 46, wherein said source is adapted to illuminate a first portion of said sample, and said image capture device is adapted to detect photoluminescence emitted from a second portion of said sample,
wherein said first portion and said second portion are at least partially overlapping, and wherein said analysis equipment further comprises an interrogation module for interrogating said image capture device repeatedly while said motion apparatus moves said sample such that said second portion is scanned across a substantial area of said sample, to acquire an image of the photoluminescence emitted from said substantial area.

50. A system according to claim 49, wherein the illumination source, the image capture device or an optical element associated with the illumination source or image capture device is capable of moving within the measurement zone.

51. A system according to claim 50 wherein motion of the illumination source, the image capture device or an optical element associated with the illumination source or image capture device is controllable to maintain a predetermined alignment with a sample.

52. A system according to claim 49, wherein said image capture device comprises a line camera or a time-delay integration camera.

53. A system according to claim 46, wherein said measurement zone comprises a shuttered or enclosed chamber.

54. A system according to claim 46, wherein said measurement zone is eye-safe without being enclosed.

55. A system according to claim 54, wherein said source comprises an eye-safe illuminator.

56. A system for conducting an analysis of a sample of a semiconductor material, comprising:
a transport mechanism configured to transport said sample to a measurement zone;
analysis equipment configured to conduct at least a photoluminescence analysis of said sample within said measurement zone, said analysis equipment comprising a source of predetermined illumination suitable for generating photoluminescence from said semiconductor material, and a multi-pixel image capture device for acquiring an image of the photoluminescence emitted from said sample; and
a motion apparatus configured to maintain motion of said sample within said measurement zone during said analysis,
wherein said system is configured to conduct an analysis of a sample of a semiconductor material comprising passivated silicon, and said source is configured to generate photoluminescence with an illumination intensity between about 0.1 and 10 W/cm$^2$.

57. A system according to claim 56, wherein said source of predetermined illumination is adapted to illuminate an area of said sample, and said image capture device is an area image capture device adapted to capture an image of said photoluminescence in an image acquisition time t,
wherein said motion apparatus is adapted to move said sample at a speed v relative to said area image capture device such that the product of the image acquisition time t (s) and the speed v (m/s) is less than a distance on said sample corresponding to one row of pixels in said area image capture device.

58. A system according to claim 57, wherein said source is adapted to provide illumination comprising a pulse of light.

59. A system according to claim 56, wherein said source is adapted to illuminate a first portion of said sample, and said image capture device is adapted to detect photoluminescence emitted from a second portion of said sample, wherein said first portion and said second portion are at least partially overlapping, and wherein said analysis equipment further comprises an interrogation module for interrogating said image capture device repeatedly while said motion apparatus moves said sample such that said second portion is scanned across a substantial area of said sample, to acquire an image of the photoluminescence emitted from said substantial area.

60. A system according to claim 59, wherein the illumination source, the image capture device or an optical element associated with the illumination source or image capture device is capable of moving within the measurement zone.

61. A system according to claim 60 wherein motion of the illumination source, the image capture device or an optical element associated with the illumination source or image capture device is controllable to maintain a predetermined alignment with a sample.

62. A system according to claim 59, wherein said image capture device comprises a line camera or a time-delay integration camera.

63. A system according to claim 56, wherein said measurement zone comprises a shuttered or enclosed chamber.

64. A system according to claim 57, wherein said measurement zone is eye-safe without being enclosed.

65. A system according to claim 64, wherein said source comprises an eye-safe illuminator.

* * * * *